United States Patent [19]

Howard et al.

[11] Patent Number: 5,721,255

[45] Date of Patent: Feb. 24, 1998

[54] SUBSTITUTED BENZYLAMINO NITROGEN CONTAINING NON-AROMATIC HETEROCYCLES

[75] Inventors: Harry R. Howard, Bristol, Conn.; Masami Nakane, Nagoya, Japan; Masaya Ikunaka, Chita, Japan; Kunio Satake, Handa, Japan; Terry J. Rosen, East Lyme, Conn.; John A. Lowe, III, Stonington, Conn.; Brian T. O'Neill, Westbrook, Conn.; Fumitaka Ito, Chita-gun, Japan

[73] Assignee: Pfizer Inc., New York, N.Y.

[21] Appl. No.: 387,765

[22] PCT Filed: May 5, 1993

[86] PCT No.: PCT/US93/04063

§ 371 Date: Feb. 15, 1995

§ 102(e) Date: Feb. 15, 1995

[87] PCT Pub. No.: WO94/04496

PCT Pub. Date: Mar. 3, 1994

[51] Int. Cl.$^6$ .................. A61K 31/445; A61K 31/47; A61K 31/40; C07D 211/56; C07D 401/12

[52] U.S. Cl. .................. 514/329; 514/212; 514/278; 514/314; 514/426; 540/543; 540/597; 540/602; 540/605; 546/16; 546/176; 546/177; 546/223; 548/495; 548/503; 548/557

[58] Field of Search .................. 546/223, 16, 177, 546/176; 548/557, 495, 503; 514/329, 426, 212, 278, 314; 540/543, 597, 602, 605

[56] References Cited

U.S. PATENT DOCUMENTS

| | | | |
|---|---|---|---|
| 5,026,858 | 6/1991 | Vega-Noverola | 546/224 |
| 5,162,339 | 11/1992 | Lowe, III | 514/305 |
| 5,232,929 | 8/1993 | Desai et al. | 514/314 |
| 5,256,671 | 10/1993 | Ladduwahetty | 514/305 |
| 5,373,003 | 12/1994 | Lowe, III | 514/216 |

FOREIGN PATENT DOCUMENTS

| | | |
|---|---|---|
| 2327192 | 12/1973 | Germany . |
| 454038 | 11/1977 | Spain . |
| WO9118899 | 12/1991 | WIPO . |
| WO9201688 | 2/1992 | WIPO . |
| WO9206079 | 4/1992 | WIPO . |
| WO9217449 | 10/1992 | WIPO . |
| WO9220676 | 11/1992 | WIPO . |
| WO9221677 | 12/1992 | WIPO . |
| WO9300330 | 1/1993 | WIPO . |
| WO9300331 | 1/1993 | WIPO . |
| WO9301170 | 1/1993 | WIPO . |
| WO9306099 | 4/1993 | WIPO . |
| WO9310073 | 5/1993 | WIPO . |

OTHER PUBLICATIONS

Vaught JL. (1988) Life Sci. 43, 1419–1431.

Delgado JN, Remers WA. Textbook of Organic Medicinal and Pharmaceutical Chemistry, Ninth Edition, p. 30, 1991.

John A. Lowe, III et al., The Discovery of (2S,3S)-cis--(Diphenylmethyl)-N-[(2-methoxyphenyl)methyl]-1-azabicyclo[2.2.2]-octan-3-amine as Novel, Nonpeptide Substance P Antagonist, J. Med. Chem., 1992, 35, 2591–2600.

Primary Examiner—C. Warren Ivy
Assistant Examiner—Evelyn Huang
Attorney, Agent, or Firm—Peter C. Richardson; Paul H. Ginsburg; B. Timothy Creagan

[57] ABSTRACT

The present invention relates to novel substituted benzylamino nitrogen containing non-aromatic heterocycles and, specifically, to compounds of the formula

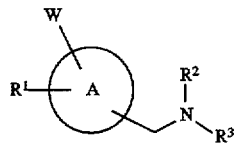

wherein W, $R^1$, $R^2$, $R^3$ and A are as defined in the specification, and to intermediates used in the synthesis of such compounds. The novel compounds of formula I are useful in the treatment of inflammatory and central nervous system disorders, as well as other disorders.

19 Claims, No Drawings

SUBSTITUTED BENZYLAMINO NITROGEN CONTAINING NON-AROMATIC HETEROCYCLES

This application is the national phase of PCT/US 93/04063, filed May 5, 1993.

BACKGROUND OF THE INVENTION

The present invention relates to novel substituted benzylamino nitrogen containing non-aromatic heterocycles, pharmaceutical compositions comprising such compounds and the use of such compounds in the treatment and prevention of inflammatory and central nervous system disorders, as well as several other disorders. The pharmaceutically active compounds of this invention are substance P receptor antagonists. This invention also relates to novel intermediates used in the synthesis of such substance P receptor antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has been shown to be involved in the transmission of pain or migraine (see B. E. B. Sandberg et al., *Journal of Medicinal Chemistry*, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

Quinuclidine, piperidine, and azanorbornane derivatives and related compounds that exhibit activity as substance P receptor antagonists are referred to in U.S. patent application Ser. No. 566,338 filed Nov. 20, 1989, U.S. patent application Ser. No. 724,268, filed Jul. 1, 1991, PCT patent application PCT/US 91/02853, filed Apr. 25, 1991, PCT patent application PCT/US 91/03369, filed May 14, 1991, PCT patent application PCT/US 91/05776, filed Aug. 20, 1991, PCT patent application PCT/US 92/00113, filed Jan. 17, 1992, PCT patent application PCT/US 92/03571, filed May 5, 1992, PCT patent application PCT/US 92/03317, filed Apr. 28, 1992, PCT patent application PCT/US 92/04697, filed Jun. 11, 1992, U.S. patent application 766,488, filed Sep. 26, 1991, U.S. patent application 790,934, filed Nov. 12, 1991, PCT patent application PCT/US 92/04002, filed May 19, 1992, and Japanese Patent Application No. 065337/92, filed Mar. 23, 1992.

SUMMARY OF THE INVENTION

The present invention relates to compounds of the formula

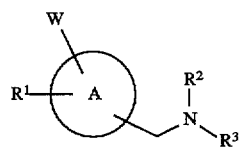

wherein ring A is an aryl group selected from phenyl, naphthyl, thienyl, dihydroquinolinyl and indolinyl, and wherein the side chain containing $NR^2R^3$ is attached to a carbon atom of ring A;

W is hydrogen, $(C_1-C_6)$alkyl, $S-(C_1-C_3)$alkyl, halo or $(C_1-C_6)$alkoxy optionally substituted with from one to three fluorine atoms;

$R^1$ is selected from amino, $(C_1-C_6)$alkylamino, di-$(C_1-C_6)$alkylamino, $-S(O)_v-(C_1-C_{10})$-alkyl wherein v is zero, one or two, $-S(O)_v$-aryl wherein v is zero, one or two, $-O$-aryl, $-SO_2NR^4R^5$ wherein each of $R^4$ and $R^5$ is, independently, $(C_1-C_6)$alkyl, or $R^4$ and $R^5$, together with the nitrogen to which they are attached, form a saturated ring containing one nitrogen and from 3 to 6 carbons,

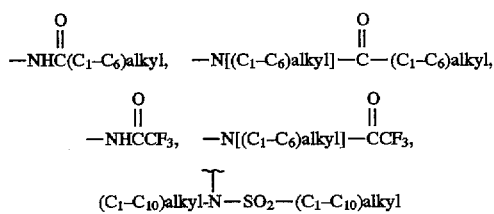

wherein one or both of the alkyl moieties may optionally be substituted with from one to three fluorine atoms, $-N(SO_2-(C_1-C_{10})alkyl)_2$ and

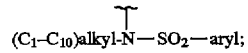

and wherein the aryl moieties of said $-S(O)_v$-aryl, $-O$-aryl and

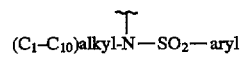

are independently selected from phenyl and benzyl and may optionally be substituted with from one to three substituents independently selected from $(C_1-C_4)$alkyl, $(C_1-C_4)$alkoxy and halo;

or $R^1$ is a group having the formula

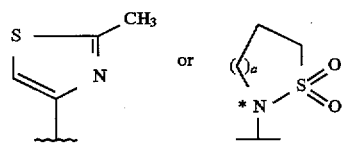

wherein a is 0, 1 or 2 and the asterisk represents a position meta to the $R^2R^3NCH_2$ side chain;

$R^2$ is hydrogen or $-CO_2(C_1-C_{10})$alkyl;

R³ is selected from

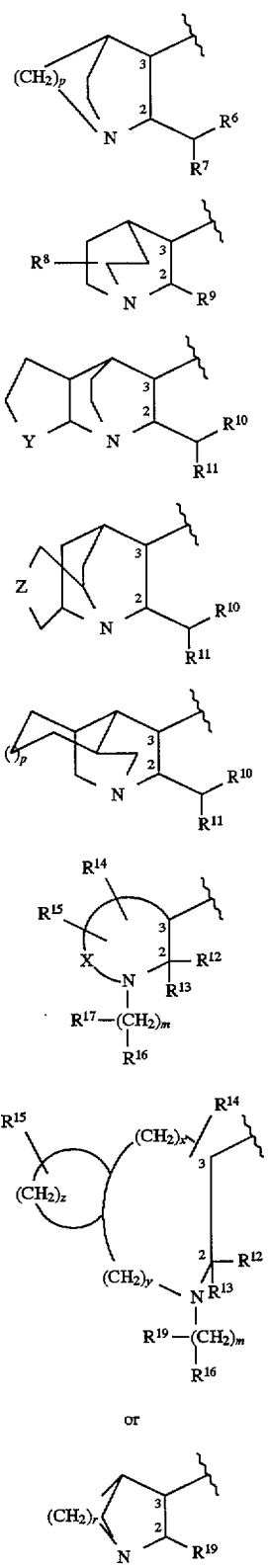

II

III

IV

V

VI

VII

VIII or

IX wherein R⁶ and R¹⁰ are independently selected from furyl, thienyl, pyridyl, indolyl, biphenyl and phenyl, wherein said phenyl may optionally be substituted with one or two substituents independently selected from halo, $(C_1-C_{10})$ alkyl optionally substituted with from one to three fluorine atoms, $(C_1-C_{10})$ alkoxy optionally substituted with from one to three fluorine atoms, carboxy, benzyloxycarbonyl and $(C_1-C_3)$ alkoxycarbonyl;

$R^7$ is selected from $(C_3-C_4)$ branched alkyl, $(C_5-C_6)$ branched alkenyl, $(C_5-C_7)$ cycloalkyl, and the radicals named in the definition of $R^6$;

$R^8$ is hydrogen or $(C_1-C_6)$ alkyl;

$R^9$ and $R^{19}$ are independently selected from phenyl, biphenyl, naphthyl, pyridyl, benzhydryl, thienyl or furyl, and $R^9$ and $R^{19}$ may optionally be substituted with from one to three substituents independently selected from halo, $(C_1-C_{10})$ alkyl optionally substituted with from one to three fluorine atoms and $(C_1-C_{10})$ alkoxy optionally substituted with from one to three fluorine atoms;

Y is $(CH_2)_l$ wherein 1 is an integer from one to three, or Y is a group of the formula

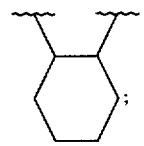

(J)

Z is oxygen, sulfur, amino, $(C_1-C_3)$alkylamino or $(CH_2)_n$ wherein n is zero, one or two;

x is zero, one or two;

y is zero, one or two;

z is three, four or five;

o is two or three;

p is zero or one;

r is one, two or three;

the ring containing $(CH_2)_z$ may contain from zero to three double bonds, and one of the carbon atoms of $(CH_2)_z$ may optionally be replaced by oxygen, sulfur or nitrogen;

$R^{11}$ is thienyl, biphenyl or phenyl optionally substituted with one or two substituents independently selected from halo, $(C_1-C_{10})$ alkyl optionally substituted with from one to three fluorine atoms and $(C_1-C_{10})$ alkoxy optionally substituted with from one to three fluorine atoms;

X is $(CH_2)_q$ wherein q is an integer from 1 to 6, and wherein any one of the carbon-carbon single bonds in said $(CH_2)_q$ may optionally be replaced by a carbon-carbon double bond, and wherein any one of the carbon atoms of said $(CH_2)_q$ may optionally be substituted with $R^{14}$, and wherein any one of the carbon atoms of said $(CH_2)_q$ may optionally be substituted with $R^{15}$;

m is an integer from 0 to 8, and any one of the carbon-carbon single bonds of $(CH_2)_m$, wherein both carbon atoms of such bond are bonded to each other and to another carbon atom of the $(CH_2)_m$ chain, may optionally be replaced by a carbon-carbon double bond or a carbon-carbon triple bond, and any one of the carbon atoms of said $(CH_2)_m$ may optionally be substituted with $R^{17}$;

$R^{12}$ is a radical selected from hydrogen, $(C_1-C_6)$ straight or branched alkyl, $(C_3-C_7)$ cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl-$(C_2-C_6)$ alkyl, benzhydryl and benzyl, wherein the point of attachment on $R^{12}$ is a carbon atom unless $R^{12}$ is hydrogen, and wherein each of said aryl and heteroaryl groups and the phenyl moieties of said benzyl, phenyl-$(C_2-C_6)$ alkyl and benzhydryl may optionally be substituted with one or more substituents independently selected from halo, nitro, $(C_1-C_{10})$ alkyl optionally substituted with from one to three fluorine atoms, $(C_1-C_{10})$ alkoxy optionally substituted with from one to three fluorine atoms, amino, hydroxy-$(C_1-C_6)$alkyl, $(C_1-C_6)$alkoxy-$(C_1-C_6)$alkyl, $(C_1-C_6)$-alkylamino,

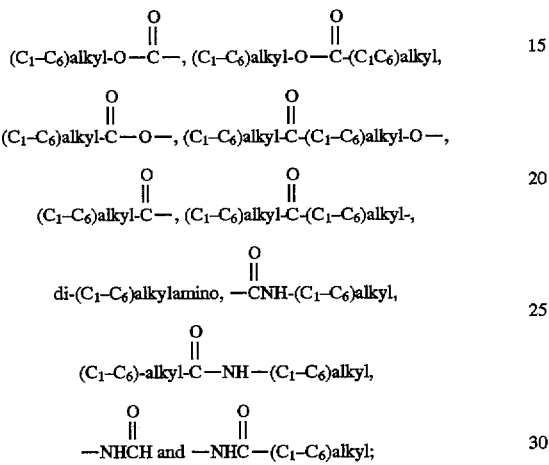

and wherein one of the phenyl moieties of said benzhydryl may optionally be replaced by naphthyl, thienyl, furyl or pyridyl;

$R^{13}$ is hydrogen, phenyl or $(C_1-C_6)$alkyl;

or $R^{12}$ and $R^{13}$, together with the carbon to which they are attached, form a saturated carbocyclic ring having from 3 to 7 carbon atoms wherein one of said carbon atoms that is neither the point of attachment of the spiro ring nor adjacent to such point of attachment may optionally be replaced by oxygen, nitrogen or sulfur;

$R^{14}$ and $R^{15}$ are each independently selected from hydrogen, hydroxy, halo, amino, oxo (=O), cyano, hydroxy-$(C_1-C_6)$alkyl, $(C_1-C_6)$alkoxy-$(C_1-C_6)$alkyl, $(C_1-C_6)$alkylamino,

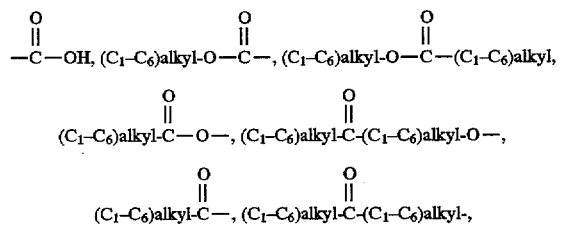

and the radicals set forth in the definition of $R^{12}$;

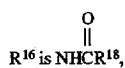

$NHCH_2R^{18}$, $SO_2R^{18}$, $CO_2H$ or one of the radicals set forth in any of the definitions of $R^{12}$, $R^{14}$ and $R^{15}$;

$R^{17}$ is oximino (=NOH) or one of the radicals set forth in any of the definitions of $R^{12}$, $R^{14}$ and $R^{15}$; and $R^{18}$ is $(C_1-C_6)$alkyl, hydrogen, phenyl or phenyl $(C_1-C_6)$ alkyl;

with the proviso that (a) when m is 0, one of $R^{16}$ and $R^{17}$ is absent and the other is hydrogen, (b) when $R^3$ is a group of the formula VIII, $R^{14}$ and $R^{15}$ cannot be attached to the same carbon atom, (c) when $R^{14}$ and $R^{15}$ are attached to the same carbon atom, then either each of $R^{14}$ and $R^{15}$ is independently selected from hydrogen, fluoro, $(C_1-C_6)$alkyl, hydroxy-$(C_1-C_6)$alkyl and $(C_1-C_6)$alkoxy-$(C_1-C_6)$alkyl, or $R^{14}$ and $R^{15}$, together with the carbon to which they are attached, form a $(C_3-C_6)$ saturated carbocyclic ring that forms a spiro compound with the nitrogen-containing ring to which they are attached; (d) when $R^1$ is amino, $(C_1-C_6)$ alkylamino, di-$(C_1-C_6)$alkylamino or

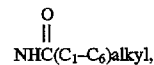

$NHC(C_1-C_6)$alkyl, $R^3$ is a group of the formula II, III, IV, V or VI, and (e) when $R^{14}$ or $R^{15}$ is attached to a carbon atom of X or $(CH_2)_y$ that is adjacent to the ring nitrogen, then $R^{14}$ or $R^{15}$, respectively, must be a substituent wherein the point of attachment is a carbon atom.

The present invention also relates to the pharmaceutically acceptable acid addition and base salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate) ]salts. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium calcium and magnesium, etc.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined as above.

The term "one or more substituents," as used herein, includes from one to the maximum number of substituents possible based on the number of available bonding sites.

Preferred compounds of the formula I include those wherein the substituents at positions "2" and "3" of the nitrogen containing ring of $R^3$ are in a cis configuration. When $R^3$ is a group of the formula VII or VIII, "a cis configuration," as used herein, means that the non-hydrogen substituent at position "3" is cis to $R^{12}$.

Other preferred compounds of the formula I are those wherein $R^3$ is a group of the formula II, III, VII or IX; $R^2$ is hydrogen; ring A is phenyl or indolinyl; W is $(C_1-C_3)$ alkoxy optionally substituted with from one to five fluorine atoms; and $R^1$ is $S(O)_v$—$(C_1-C_{10})$alkyl wherein v is zero, one or two, $S(O)_v$-aryl wherein v is zero, one or two, O-aryl, $$(C_1-C_{10})\text{alkyl-N}-SO_2-(C_1-C_{10})\text{alkyl}$$

wherein one or both of the alkyl moieties may optionally be substituted with from one to three fluorine atoms, —N(SO$_2$-(C$_1$–C$_{10}$)alkyl)$_2$ or $$(C_1-C_{10})\text{alkyl-N}-SO_2\text{-aryl}$$

wherein said aryl is phenyl or benzyl and may optionally be substituted with from one to three substituents independently selected from (C$_1$–C$_4$)alkyl, (C$_1$–C$_4$)alkoxy and halo.

More preferred compounds of the formula I are the foregoing preferred compounds wherein: (a) R$^3$ is a group of the formula III and R$^9$ is benzhydryl; (b) R$^3$ is a group of the formula VII, each of R$^{13}$, R$^{14}$, R$^{15}$ and R$^{16}$ is hydrogen, m is zero and X is —(CH$_2$)$_3$—; or (c) R$^3$ is a group of the formula IX, r is two and R$^{19}$ is benzhydryl.

Other more preferred compounds of the formula I are those wherein: (a) R$^3$ is a group of the formula III wherein the substituents at positions "2" and "3" of the nitrogen containing ring are in the cis configuration, R$^9$ is benzhydryl and ring A is phenyl; (b) R$^3$ is a group of the formula VII wherein R$^{12}$ and the substituent at position "3" of the nitrogen containing ring are in the cis configuration, ring A is phenyl, R$^{12}$ is phenyl, each of R$^2$, R$^{13}$, R$^{14}$, R$^{15}$ and R$^{16}$ is hydrogen, m is zero, W is methoxy or isopropoxy, X is —(CH$_2$)$_3$— and R$^1$ is $S(O)_v$—(C$_1$–C$_{10}$)alkyl wherein v is zero, one or two, or $$(C_1-C_{10})\text{alkyl-N}-SO_2-(C_1-C_{10})\text{alkyl};$$

or (c) R$^3$ is a group of the formula IX wherein the substituents at positions "2" and "3" of the nitrogen containing ring are in the cis configuration, R$^{19}$ is benzhydryl, r is two and ring A is phenyl.

Especially preferred compounds of the formula I are those wherein R$^3$ is a group of the formula III, R$^9$ is benzhydryl, ring A is phenyl, W is selected from OCF$_3$, isopropoxy, OCH$_3$, OCHF$_2$ and OCH$_2$CF$_3$, and R$^1$ is selected from amino, (C$_1$–C$_6$)alkylamino, di-(C$_1$–C$_6$)alkylamino, and —S(O)$_v$—(C$_1$–C$_{10}$)alkyl wherein v is zero, one or two.

Other especially preferred compounds of this invention are those wherein R$^3$ is a group of the formula VII, each of R$^{13}$, R$^{14}$, R$^{15}$ and R$^{16}$ is hydrogen, m is zero, X is —(CH$_2$)$_3$—, ring A is phenyl, W is selected from OCF$_3$, OCH$_3$, isopropoxy, OCHF$_2$ and OCH$_2$CF$_3$, and R$^1$ is selected from —S(O)$_v$—(C$_1$–C$_{10}$)alkyl wherein v is zero, one or two, and $$(C_1-C_{10})\text{alkyl-N}-SO_2-(C_1-C_{10})\text{alkyl}.$$

Specific preferred compounds of the formula I include the following:

(2S,3S)-3-[2-methoxy-5-(N-acetyl-N-methylamino) benzylamino]-2-diphenylmethyl-1-azabicyclo[2.2.2] octane;

(1SR,2SR,3SR,4RS)-3-(2-methoxy-5-(N-methyl-N-trifluoromethane-sulfonylamino)benzyl)amino-2-benzhydryl-[2.2.1]-azanorbornane;

(1SR,2SR,3SR,4RS)-3-[2-methoxy-5-(N-thiazolidine-S, S-dioxide)benzyl]amino-2-benzhydryl-[2.2.1]-1-azanorbornane;

(1SR,2SR,3SR,4RS)-3-[(2,3-dihydro-5-methoxy-1-methanesulfonyl-6-indolyl)methylamino]-2-benzhydryl-[2.2.1]-1-azanorbornane;

(2S,3S)-3-(2-methoxy-5-methylthiobenzyl)amino-2-phenylpiperidine;

(2S,3S)-3-(2-methoxy-5-methylsulfonylbenzyl)amino-2-phenylpiperidine;

(2S,3S)-3-[2-methoxy-5-(N-methyl-N-methanesulfonylamino)-benzyl]amino-2-phenylpiperidine;

(2S,3S)-3-[2-trifluoromethoxy-5-(N-methyl-N-methanesulfonylamino)benzyl]amino-2-phenylpiperidine;

(2S,3S)-3-[2-isopropoxy-5-(N-methyl-N-methanesulfonyl-amino)benzyl]amino-2-phenylpiperidine;

(2S,3S)-3-[2-methoxy-5-(N-isopropyl-N-methanesulfonyl-amino)benzyl]amino-2-phenylpiperidine;

(2S,3S)-3-[2-isopropoxy-5-(N-isopropyl-N-methanesulfonyl-amino)benzyl]amino-2-phenylpiperidine;

(2S,3S)-3-[2-isopropoxy-5-(N-isopropyl-N-methanesulfonyl-amino)benzyl]amino-2-phenylpiperidine;

(2S,3S)-3-[2-methoxy-5-(N-cyclopentyl-N-methanesulfonyl-amino)benzyl]amino-2-phenylpiperidine;

(2S,3S)-3-[2-methoxy-5-(N-methyl-N-trifluoromethane-sulfonylamino)benzyl]amino-2-phenylpiperidine;

(2S,3S)-3-[2-isopropoxy-5-(N-methyl-N-trifluoromethane-sulfonylamino)benzyl]amino-2-phenylpiperidine;

(2S,3S)-3-[2-methoxy-5-(N-methyl-N-isopropylsulfonylamino)-benzyl]amino-2-phenylpiperidine;

(2S,3S)-3-[2-methoxy-5-(N-thiazolidine-S,S-dioxide)-benzyl]amino-2-phenyl-piperidine;

(2S,3S)-3-[(2,3-dihydro-5-methoxy-1-methanesulfonyl-6-indolyl)methylamino]-2-phenylpiperidine;

(2S,3S)-3-[(2,3-dihydro-5-methoxy-2-methyl-1-methane-sulfonyl-6-indolyl)methylamino]-2-phenylpiperidine;

(2SR,3SR,4RS)-2-benzhydryl-4-(2-hydroxyethyl)-3-(2-methoxy-5-methylthiobenzyl)aminopyrrolidine;

(2SR,3SR,4RS)-2-benzhydryl-4-(2-hydroxyethyl)-3-(2-methoxy-5-(N-methyl-N-methanesulfonylamino) benzyl)aminopyrrolidine;

(2SR,3SR,4RS)-2-benzhydryl-4-(2-hydroxyethyl)-3-(2-methoxy-5-(N,thiazolidine-S,S-dioxide)benzyl) aminopyrrolidine;

(2S,3S)-N-(2-methoxy-5-methylthiophenyl)methyl-2-diphenylmethyl-1-azabicyclo[2.2.2]octan-3-amine;

(2S,3S)-N-(2-methoxy-5-dimethylaminophenyl)methyl-2-diphenylmethyl-1-azabicyclo[2.2.2]octan-3-amine;

(2S,3S)-N-(5-ethylthio-2-methoxyphenyl)methyl-2-diphenylmethyl-1-azabicyclo[2.2.2]octan-3-amine;

(2S,3S)-N-(5-trifluoroacetylamino-2-methoxyphenyl) methyl-2-diphenylmethyl-1-azabicyclo[2.2.2]octan-3-amine;

(2S,3S)-N-(5-amino-2-methoxyphenyl)methyl-2-diphenylmethyl-1-azabicyclo[2.2.2]octan-3-amine;

(2S,3S)-N-(2-methoxy-5-methylsulfinylphenyl)methyl-2-diphenylmethyl-1-azabicyclo[2.2.2]octan-3-amine; and (2S,3S)-N-(2-methoxy-5-methylsulfonylphenyl)methyl-2-diphenylmethyl-1-azabicyclo[2.2.2]octan-3-amine.
Other compounds of the formula I include:

4-(2-methylthiophenyl)methylamino-3-phenyl-2-azabicyclo[3.3.0]octane;

4-benzhydryl-5-(2-methylthiophenyl)methylamino-3-azabicyclo[4.1.0]heptane;

4-(2-methylthiophenyl)methylamino-3-phenyl-2-azabicyclo[4.4.0]decane;

8-benzhydryl-7-(2-methylthio-5-trifluoromethoxyphenyl)methylamino-9-azatricyclo[4.3.1.0$^{4,9}$]decane;

9-benzhydryl-8-(2-methylthio-5-trifluoromethoxyphenyl)methylamino-10-azatricyclo[4.4.1.0$^{5,10}$]undecane;

9-benzhydryl-8-(2-methylthio-5-trifluoromethoxyphenyl)methylamino-3-thia-10-azatricyclo[4.4.1.0$^{5,10}$]undecane;

2-benzhydryl-3-(2-methylthiophenyl)methylamino-5,6-pentamethylene-quinuclidine;

2-benzhydryl-3-(2-methylthiophenyl)methylamino-5,6-trimethylene-quinuclidine;

cis-3-(2-phenoxyphenyl)methylamino-2-benzhydrylquinuclidine;

8-benzhydryl-9-(2-methylthiophenyl)methylamino-7-azatricyclo[4.4.1.0$^{5,10}$]undecane;

2-benzhydryl-3-(2-methylthiophenyl)methylamino-1-azabicyclo[3.2.2]nonane;

2-benzhydryl-3-(2-methylthiophenyl)methylamino-1-azabicyclo[2.2.1]heptane;

3-(2-methylthiophenyl)methylamino-2-phenyl-1-azabicyclo[2.2.1]heptane;

N-[3-(4-benzhydryl-1-azabicyclo[2.2.1]hept-3-ylaminomethyl)-4-methoxyphenyl]-N-isopropylisopropylsulfonamide;

N-[3-(7-benzhydryl-1-azabicyclo[3.2.2]non-6-ylaminomethyl)-4-methoxyphenyl]-N-methylmethanesulfonamide;

N-[3-(7-benzhydryl-1-azabicyclo[3.2.2]non-6-ylaminomethyl)-4-trifluoromethoxyphenyl]-N-methylmethanesulfonamide;

N-[3-(8-benzhydryl-1-azabicyclo[4.2.2]dec-7-ylaminomethyl)-4-methoxyphenyl]-N-methylmethanesulfonamide;

N-[3-(8-benzhydryl-1-azabicyclo[4.2.2]dec-7-ylaminomethyl)-4-trifluoromethoxyphenyl]-N-methylmethanesulfonamide;

N-[3-(4-benzhydryl-1-azabicyclo[2.2.1]hept-3-ylaminomethyl)-4-methoxyphenyl]-N-methylisopropylsulfonamide;

N-[3-(4-benzhydryl-1-azabicyclo[2.2.1]hept-3-ylaminomethyl)-4-methoxyphenyl]-N-isopropyltrifluoromethanesulfonamide;

N-[3-(4-benzhydryl-1-azabicyclo[2.2.1]hept-3-ylaminomethyl)-4-methoxyphenyl]-isopropylsulfone;

N-[3-(4-benzhydryl-1-azabicyclo[2.2.1]hept-3-ylaminomethyl)-4-methoxyphenyl]-methylsulfone;

N-[3-(2-benzhydryl-1-azabicyclo[2.2.2]oct-3-ylaminomethyl)-4-methoxyphenyl]-N-methylmethanesulfonamide;

N-[3-(2-benzhydryl-1-azabicyclo[2.2.2]oct-3-ylaminomethyl)-4-isopropoxyphenyl]-N-methylmethanesulfonamide;

N-[3-(2-benzhydryl-1-azabicyclo[2.2.2]oct-3-ylaminomethyl)-4-trifluoromethoxyphenyl]-N-methylmethanesulfonamide;

N-[3-(2-benzhydryl-1-azabicyclo[2.2.2]oct-3-ylaminomethyl)-4-methoxyphenyl]-N-isopropylmethanesulfonamide;

N-[3-(2-benzhydryl-1-azabicyclo[2.2.2]oct-3-ylaminomethyl)-4-methoxyphenyl]-N-methyltrifluoromethanesulfonamide;

N-[3-(2-benzhydryl-1-azabicyclo[2.2.2]oct-3-ylaminomethyl)-4-methoxyphenyl]-methanesulfone;

N-[3-(2-benzhydryl-1-azabicyclo[2.2.2]oct-3-ylaminomethyl)-4-trifluoromethoxyphenyl]-methanesulfone;

N-[3-(2-benzhydryl-1-azabicyclo[2.2.2]oct-3-ylaminomethyl)-4-methoxyphenyl]-isopropylsulfone;

N-[3-(9-benzhydryl-1-azatricyclo[5.2.2.0$^{2,6}$]undec-8-ylaminomethyl)-4-methoxyphenyl]-N-methylmethanesulfonamide;

N-[3-(9-benzhydryl-1-azatricyclo[5.2.2.0$^{2,6}$]undec-8-ylaminomethyl)-4-isopropoxyphenyl]-N-methylmethanesulfonamide;

N-[3-(9-benzhydryl-1-azatricyclo[5.2.2.0$^{2,6}$]undec-8-ylaminomethyl)-4-trifluoromethoxyphenyl]-N-methylmethanesulfonamide;

N-[3-(10-benzhydryl-octahydro-1,4-ethano-quinolin-9-ylaminomethyl)-4-isopropoxyphenyl]-N-isopropylmethanesulfonamide;

N-[3-(9-benzhydryl-1-azatricyclo[5.2.2.0$^{2,6}$]undec-8-ylaminomethyl)-4-methoxyphenyl]-N-isopropylmethanesulfonamide;

N-[3-(9-benzhydryl-1-azatricyclo[5.2.2.0$^{2,6}$]undec-8-ylaminomethyl)-4-methoxyphenyl]-N-methylisopropylsulfonamide;

N-[3-(9-benzhydryl-1-azatricyclo[5.2.2.0$^{2,6}$]undec-8-ylaminomethyl)-4-methoxyphenyl]-methanesulfone;

N-[3-(9-benzhydryl-1-azatricyclo[5.2.2.0$^{2,6}$]undec-8-ylaminomethyl)-4-trifluoromethoxyphenyl]-methanesulfone;

N-[3-(9-benzhydryl-1-azatricyclo[5.2.2.0$^{2,6}$]undec-8-ylaminomethyl)-4-methoxyphenyl]-isopropylsulfone;

N-[3-(9-benzhydryl-8-azatricyclo[5.3.1.0$^{3,8}$]undec-10-ylaminomethyl)-4-methoxyphenyl]-N-methylmethanesulfonamide;

N-[3-(10-benzhydryl-9-azatricyclo[6.3.1.0$^{3,9}$]dodec-11-ylaminomethyl)-4-methoxyphenyl]-N-methylmethanesulfonamide;

N-[3-(9-benzhydryl-8-azatricyclo[5.3.1.0$^{3,8}$]undec-10-ylaminomethyl)-4-methoxyphenyl]-N-isopropylmethanesulfonamide;

N-[3-(10-benzhydryl-9-azatricyclo[6.3.1.0$^{3,9}$]dodec-11-ylaminomethyl)-4-methoxyphenyl]-N-isopropylmethanesulfonamide;

N-[3-(10-benzhydryl-9-azatricyclo[6.3.1.0$^{3,9}$]dodec-11-ylaminomethyl)-4-methoxyphenyl]-N-methylisopropylsulfonamide;

N-[3-(11-benzhydryl-1-azatricyclo[6.3.1.0$^{3,9}$]dodec-10-ylaminomethyl)-4-methoxyphenyl]-N-methylmethanesulfonamide;

N-[3-(11-benzhydryl-1-azatricyclo[6.3.1.0$^{3,9}$]dodec-10-ylaminomethyl)-4-methoxyphenyl]-N-methylmethanesulfonamide;

N-[3-(11-benzhydryl-1-azatricyclo[6.3.1.0$^{3,9}$]dodec-10-ylaminomethyl)-4-methoxyphenyl]-N-methylisopropylsulfonamide;

N-[3-(11-benzhydryl-1-azatricyclo[6.3.1.0³,⁹]dodec-10-ylaminomethyl)-4-methoxyphenyl]-N-methyl-trifluoromethanesulfonamide;

N-[3-(3-benzhydryl-octahydro-2,5-methano-isoquinolin-4-ylaminomethyl)-4-methoxyphenyl]-N-methyl-methanesulfonamide;

N-[3-(3-benzhydryl-octahydro-2,5-methano-isoquinolin-4-ylaminomethyl)-4-methoxyphenyl]-N-isopropyl-methanesulfonamide;

(2-trifluoromethoxy-5-methylsulfonylbenzyl)-(2-phenylpiperidin-3-yl)-amine;

(2-difluoromethoxy-5-methylsulfonylbenzyl)-(2-phenylpiperidin-3-yl)-amine;

(2-cyclopropoxy-5-methylsulfonylbenzyl)-(2-phenylpiperidin-3-yl)-amine;

(2-cyclopentyloxy-5-methylsulfonylbenzyl)-(2-phenylpiperidin-3-yl)-amine;

(2-isopropoxy-5-methylsulfonylbenzyl)-(2-phenylpiperidin-3-yl)-amine;

(2-methoxy-5-isopropylsulfonylbenzyl)-(2-phenylpiperidin-3-yl)-amine;

N-[4-methoxy-3-(3-phenyl-decahydro-isoquinolin-4-ylaminomethyl)-phenyl]-N-methyl-methanesulfonamide;

N-[4-trifluoromethoxy-3-(3-phenyl-decahydroisoquinolin-4-ylaminomethyl)-phenyl]-N-methyl-methanesulfonamide;

N-[4-methoxy-3-(3-phenyl-decahydro-isoquinolin-4-ylaminomethyl)-phenyl]-N-isopropyl-methanesulfonamide;

N-[4-methoxy-3-(2-phenyl-decahydro-quinolin-3-ylaminomethyl)-phenyl]-N-methyl-methanesulfonamide;

N-[4-methoxy-3-(2-phenyl-decahydro-quinolin-3-ylaminomethyl)-phenyl]-N-isopropyl-methanesulfonamide;

N-[4-methoxy-3-(2-phenyl-decahydro-quinolin-3-ylaminomethyl)-phenyl]-N-methyl-isopropylsulfonamide;

N-[4-methoxy-3-(2-phenyl-octahydro-[1]pyrindin-3-ylaminomethyl)-phenyl]-N-methyl-methanesulfonamide;

N-[4-methoxy-3-(2-phenyl-octahydro-[1]pyrindin-3-ylaminomethyl)-phenyl]-N-isopropyl-methanesulfonamide;

N-[4-methoxy-3-(2-phenyl-octahydro-[1]pyrindin-3-ylaminomethyl)-phenyl]-N-methyl-trifluoromethanesulfonamide;

N-[4-methoxy-3-(2-phenyl-decahydro-cyclohepta-[b]pyridin-3-ylaminomethyl)-phenyl]-N-methyl-methanesulfonate;

N-[4-methoxy-3-(2-phenyl-octahydro-indol-3-ylaminomethyl)-phenyl]-N-methyl-methanesulfonate;

N-[-3-(2-benzhydryl-decahydro-cyclohepta[b]pyridin-3-ylaminomethyl)-4-methoxyphenyl]-N-methyl-methanesulfonate;

N-[3-(7-benzhydryl-1-aza-bicyclo[3.2.1]oct-6-ylaminomethyl)-4-methoxyphenyl]-N-methyl-methanesulfonamide;

N-[3-(7-benzhydryl-1-aza-bicyclo[3.2.1]oct-6-ylaminomethyl)-4-methoxyphenyl]-N-isopropyl-methanesulfonamide;

N-[3-(7-benzhydryl-1-aza-bicyclo[3.2.1]oct-6-ylaminomethyl)-4-methoxyphenyl]-N-methyl-isopropylsulfonamide;

N-[3-(7-benzhydryl-1-aza-bicyclo[3.2.1]oct-6-ylaminomethyl)-4-methoxyphenyl]-N-methyl-trifluoromethane-sulfonamide;

N-[3-(8-benzhydryl-1-aza-bicyclo[4.2.1]non-7-ylaminomethyl)-4-methoxyphenyl]-N-methyl-methanesulfonamide;

N-[3-(8-benzhydryl-1-aza-bicyclo[4.2.1]non-7-ylaminomethyl)-4-methoxyphenyl]-N-isopropyl-methanesulfonamide;

N-[3-(9-benzhydryl-1-aza-bicyclo[5.2.1]dec-8-ylaminomethyl)-4-methoxyphenyl]-N-isopropyl-methanesulfonamide;

N-[3-(9-benzhydryl-1-aza-bicyclo[5.2.1]dec-8-ylaminomethyl)-4-methoxyphenyl]-N-methyl-isopropylsulfonamide;

N-[3-(9-benzhydryl-1-aza-bicyclo[5.2.1]dec-8-ylaminomethyl)-4-methoxyphenyl]-methanesulfone; and N-[3-(9-benzhydryl-1-aza-bicyclo[5.2.1]dec-8-ylaminomethyl)-4-trifluoromethoxyphenyl]-methanesulfone.

The present invention also relates to compounds of the formulae

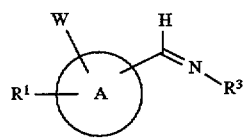

and

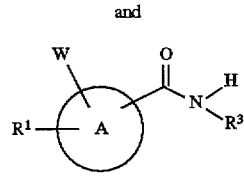

wherein ring A, $R^1$, $R^3$ and W are defined as above. These compounds are intermediate in the synthesis of compounds of the formula I.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formula I have chiral centers and therefore exist in different enantiomeric forms. This invention relates to all optical isomers and all stereoisomers of compounds of the formula I, and mixtures thereof.

DETAILED DESCRIPTION OF THE INVENTION

The compounds of the formula I may be prepared as described in the following reaction schemes and discussion. Unless otherwise indicated, ring A, W, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, X, Z, Y, m, n, o, p, q, r, x, y, and z, and structural formulas I, II, III, IV, V, VI, VII, VIII, IX, XI and XII in the reaction schemes and discussion that follow are defined as above.

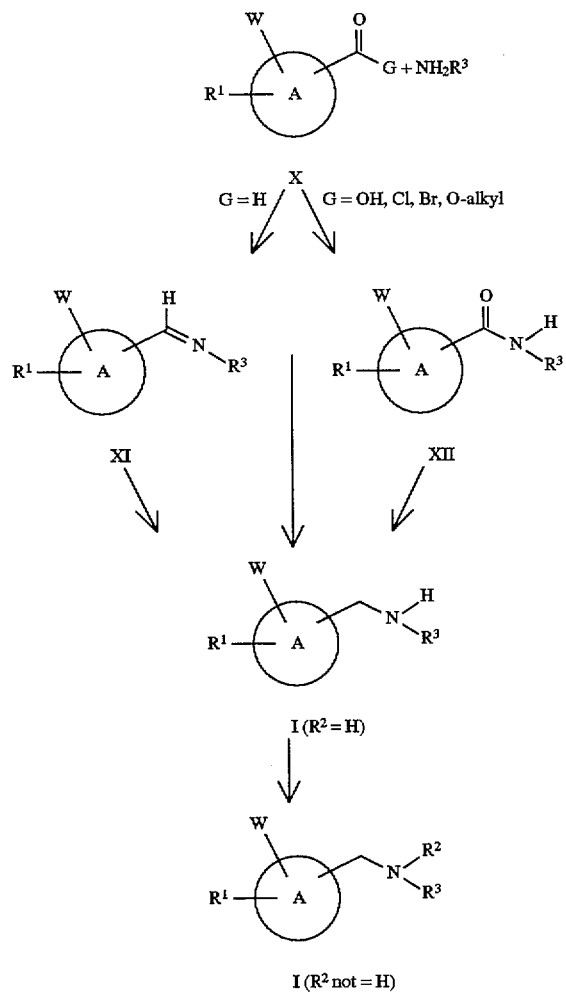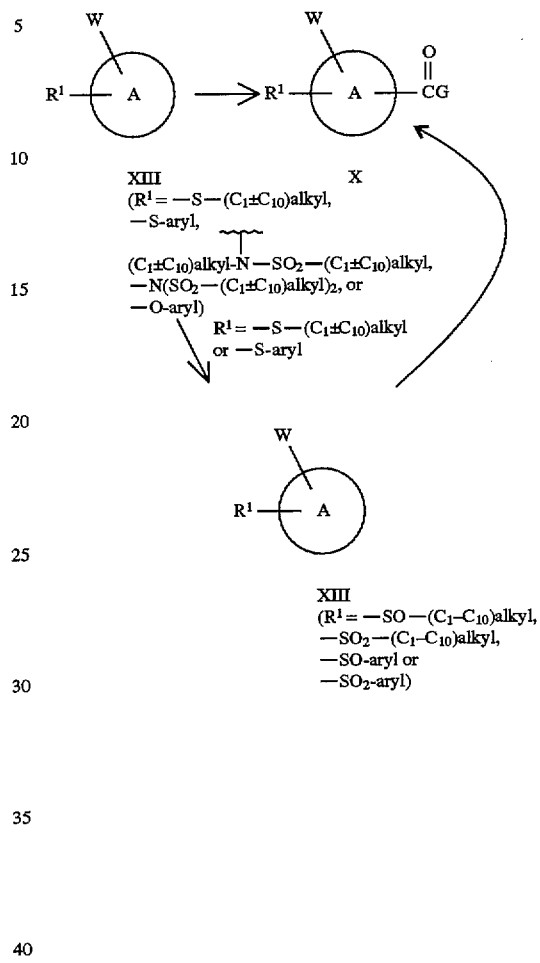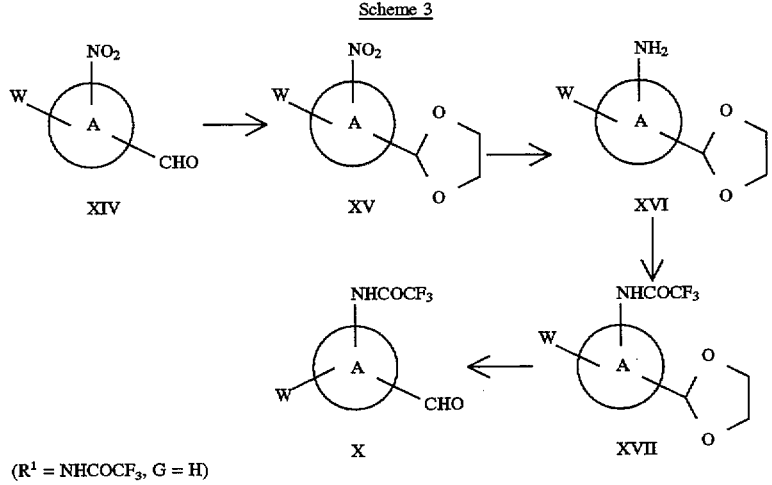

Scheme 4

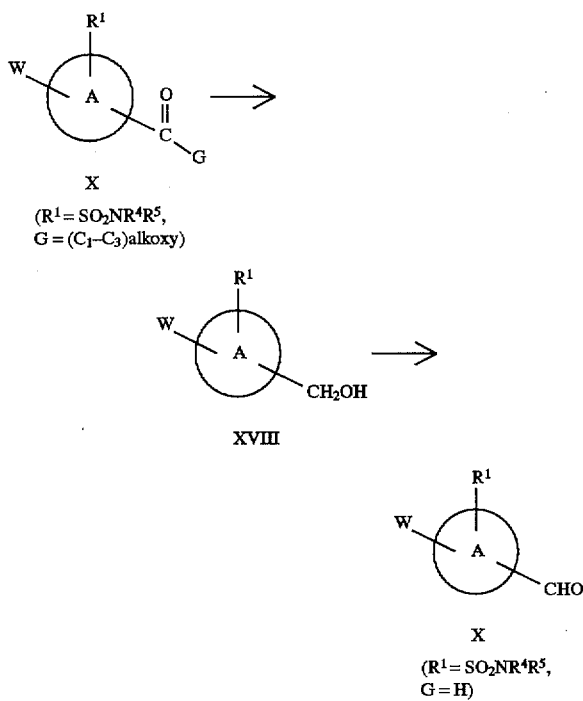

Scheme 1 illustrates the preparation of compounds of the formula I from starting materials of the formula X wherein G is hydrogen, hydroxy, chloro, bromo or $(C_1-C_6)$alkoxy.

Referring to scheme 1, a compound of the formula X wherein G is hydrogen may be converted directly into the corresponding compound of the formula I by reacting it with a compound of the formula $NH_2R^3$ in the presence of a reducing agent. Reducing agents that may be used include sodium cyanoborohydride, sodium triacetoxyborohydride, sodium borohydride, hydrogen and a metal catalyst, zinc and hydrochloric acid, and formic acid. This reaction is typically conducted in a reaction inert solvent at a temperature from about 0° C. to about 150° C. Suitable reaction inert solvents include lower alcohols (e.g., methanol, ethanol and isopropanol), 1,2-dichloroethane, acetic acid and tetrahydrofuran (THF). Preferably, the solvent is acetic acid, the temperature is about 25° C., the reducing agent is sodium triacetoxyborohydride, and the reaction is conducted in the presence of a dehydrating agent such as molecular sieves.

Alternatively, the reaction of a compound of the formula X with a compound of the formula $NH_2R^3$ may be carried out in the presence of a dehydrating agent or using an apparatus designed to remove azeotropically the water generated, to produce an imine of the formula

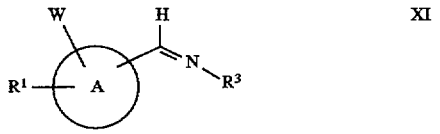

which is then reacted with a reducing agent as described above, preferably with sodium triacetoxyborohydride in an acetic acid or 1,2-dichloroethane solvent at about room temperature. The preparation of the imine is generally carried out in a reaction inert solvent such as benzene, xylene or toluene, preferably toluene, at a temperature from about 25° C. to about 110° C., preferably at about the reflux temperature of the solvent. Suitable dehydrating agents/solvent systems include titanium tetrachloride/dichloromethane titanium isopropoxide/dichloromethane and molecular sieves/THF. Titanium tetrachloride/dichloromethane is preferred.

Compounds of the formula X wherein G is hydroxy, chloro, bromo or $(C_1-C_6)$alkoxy may be converted into the corresponding compounds of formula XII having the desired $R^3$ group by reacting them with the appropriate compound of the formula $NH_2R^3$ under conditions that will be obvious to those skilled in the art, and then reducing the resulting amides to yield the desired compounds having formula I wherein $R^2$ is hydrogen. When G is hydroxy, the compound of formula X is reacted with $NH_2R^3$ in the presence of an activating agent. Appropriate activating agents include carbonyldiimidazole, diethylphosphoryl cyanide and dicyclohexylcarbodiimide. Carbonyldiimidazole is preferred. This reaction is generally conducted at a temperature from about 0° C. to about 50° C., preferably at about 25° C., in an inert solvent such as chloroform, diethyl ether, THF or dimethylformamide (DMF).

When G is chloro or bromo, the reaction of the compound of formula X with the appropriate compound of formula $NH_2R^3$ is typically carried out in the presence of an acid scavenger in an aprotic solvent at a temperature from about 0° C. to about 100° C. Suitable acid scavengers include triethylamine (TEA), pyridine and inorganic salts such as sodium and potassium carbonate. Suitable solvents include methylene chloride ($CH_2Cl_2$), chloroform ($CHCl_3$), benzene, toluene and tetrahydrofuran (THF). Preferably, the reaction is conducted in $CH_2Cl_2$ at room temperature using TEA as the acid scavenger.

When G is O—$(C_1-C_6)$alkyl, the reaction of the compound of formula $NH_2R^3$ is usually conducted in an aprotic solvent such as benzene, toluene, chlorobenzene or xylenes, at a temperature from about 25° C. to about 100° C., preferably at about the reflux temperature of the solvent.

Reduction of the compound of formula XII so formed yields the corresponding compound of the formula I wherein $R^2$ is hydrogen. This is generally accomplished using a reducing agent such as lithium aluminum hydride, borane dimethylsulfide complex or diborane, in an aprotic solvent such as THF, dioxane or diethyl ether, at a temperature from about 0° C. to about 70° C. Preferably, the reducing agent is borane dimethylsulfide complex and the reaction is carried out at about room temperature in an ethereal solvent such as THF.

Compounds of the formula I wherein $R^2$ is hydrogen may be converted into the corresponding compounds wherein $R^2$ is —$CO_2(C_1-C_{10})$alkyl by reacting them with a $(C_1-C_{10})$ alkyl halo carbonate such as methyl or ethyl chloroformate in the presence of an acid scavenger. Typically, this reaction is conducted in an polar solvent such as chloroform, methylene chloride, water or a water/acetone mixture, at a temperature from about 0° C. to about 100° C., preferably at about room temperature. Suitable acid scavengers include triethylamine, pyridine and potassium and sodium carbonate or bicarbonate.

When $R^3$ is a group of the formula II, the starting materials of the formula $NH_2R^3$ may be prepared as described in U.S. patent application Ser. No. 556,338, filed Jul. 20, 1990, which issued as U.S. Pat. No. 5,162,339, issued Nov. 10, 1992. This application is incorporated herein in its entirety.

When $R^3$ is a group of the formula III, the starting materials of the formula $NH_2R^3$ may be prepared as described in U.S. patent application Ser. No. 532,525, filed Jun. 1, 1990, which was filed as PCT patent application PCT/US 91/02853, filed Apr. 25, 1991, which was filed as U.S. National patent application Ser. No. 07/955,733, filed Dec. 1, 1992, which issued as U.S. Pat. No. 5,451,586, issued Sep. 19, 1995. Both these applications are incorporated herein in their entirety.

When $R^3$ is a group of the formula IV, V or VI, the starting materials of the formula $NH_2R^3$ may be prepared as described in U.S. patent application Ser. No. 557,442, filed Jul. 23, 1990, which was filed as PCT patent application PCT/US 91/03369, filed May 14, 1991, which was filed as U.S. National application Ser. No. 07/988,125, filed Feb. 1, 1993, which issued as U.S. Pat. No. 5,422,354, issued Jun. 6, 1995. Both these applications are incorporated herein in their entirety.

When $R^3$ is a group of the formula VII, the starting materials of the formula $NH_2R^3$ may be prepared as described in U.S. patent application Ser. No. 724,268, filed Jul. 1, 1991, which issued as U.S. Pat. No. 5,232,929, issued Aug. 3, 1993; U.S. patent application Ser. No. 800,667, filed Nov. 27, 1991, which issued as U.S. Pat. No. 5,364,943, issued Nov. 15, 1994; and PCT patent application PCT/US 92/00065, filed Jan. 14, 1992, which published as WO 92/17449, published Oct. 15, 1992, and which was filed as pending U.S. National application Ser. No. 08/119,149, filed Sep. 20, 1993. These applications are incorporated herein in their entirety.

When $R^3$ is a group of the formula VIII, the starting materials of the formula $NH_2R^3$ may be prepared as described in PCT patent application PCT/US 91/05776, filed Aug. 20, 1991, which published as WO 92/06079, published Apr. 16, 1992; U.S. patent application Ser. No. 800,667, filed Nov. 27, 1991, which issued as U.S. Pat. No. 5,364,943, issued Nov. 15, 1994; and PCT patent application PCT/US 92/00065, filed Jan. 14, 1992, which published as WO 92/17449, published Oct. 15, 1992 and which was filed as pending U.S. National application Ser. No. 08/119,149, filed Sep. 20, 1993. These applications are incorporated herein in their entirety.

When $R^3$ is a group of the formula IX, the starting materials of the formula $NH_2R^3$ may be prepared as described in U.S. patent application Ser. No. 719,884, filed Jun. 21, 1991, which was filed as International patent application PCT/US92/04697, filed Jun. 11, 1992, and published as WO 93/00330, published Jan. 7, 1993, and was filed as U.S. National patent application Ser. No. 08/167, 851, filed Dec. 14, 1994, which issued as U.S. Pat. No. 5,604,252, issued Feb. 18, 1997. This application is incorporated herein in its entirety.

Scheme 2 illustrates the preparation of the starting materials of formula X wherein G is hydrogen and $R^1$ is other than

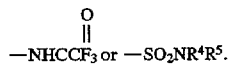

Once formed, these compounds can be converted into the corresponding compounds of the formula I or XI according to the procedures described above.

Referring to scheme 2, a compound of the formula XIII wherein $R^1$ is other than

or $-SO_2NR^4R^5$ is reacted with titanium tetrachloride ($TiCl_4$) and dichloromethyl methyl ether ($CHCl_2-O-CH_3$) at a temperature from about 0° C. to about room temperature in a methylene chloride solvent to yield the corresponding aldehyde of formula X wherein G is hydrogen. Alternatively, the compound of the formula XIII may be reacted with hexamethylene tetraamine and trifluoroacetic acid at about 70° C. to yield the same product.

Those compounds of the formula XIII wherein $R^1$ is $-SO-(C_1-C_{10})$alkyl, $-SO_2-(C_1-C_{10})$alkyl, $-SO$-aryl or $-SO_2$-aryl may be obtained from their deoxygenated counterparts of the formula XIII wherein $R^1$ is $-S-(C_1-C_{10})$alkyl or $-S$-aryl by reacting them with an oxidizing agent. For example, such oxidation may be carried out using metachloroperbenzoic acid in methylene chloride at about room temperature. It may also be carried out using peroxyphthalic acid magnesium hydrate in aqueous ethanol at a temperature from about 70° C. to about 100° C. The foregoing oxidation reactions produce mixtures of the oxy and dioxy products ($-SO-$ and $-SO_2-$) which can be separated by ordinary means.

Compounds of the formula X wherein G is hydrogen and $R^1$ is $-NHCOCF_3$ may be obtained using procedures known to those skilled in the art. Scheme 3 illustrates one method of preparing such compounds. Referring to scheme 3, the $-CHO$ group of a nitro benzaldehyde of the formula XIV is protected by conversion to the corresponding 1,3-dioxolane of formula XV. This reaction is generally carried out by heating a mixture of the nitrobenzaldehyde and ethylene glycol in an inert solvent such as benzene or toluene, preferably in the presence of an acid such as p-toluenesulfonic acid, and preferably at the reflux temperature of the solvent to remove the water formed in the reaction. The resulting compound of formula XV is then treated with hydrogen gas and a metal catalyst such as palladium on carbon in a reaction inert solvent such as ethyl acetate or a lower alcohol to convert the $NO_2$ group to an $NH_2$ group and produce the corresponding compound of formula XVI.

The resulting intermediate of formula XVI is then acylated with a reagent such as ethyl trifluoroacetate in methanol or trifluoroacetic anhydride in methylene chloride at a temperature from about 0° C. to about 50° C., preferably at about room temperature, to produce the corresponding trifluoroacetamide of the formula XVII. Treatment of this amide with a mixture of aqueous hydrochloric acid in acetone at a temperature from about 0° C. to about 50° C., preferably at room temperature, will convert the dioxolane to the desired compound of formula X wherein $R^1$ is $NHCOCF_3$ and G is hydrogen.

Scheme 4 illustrates the preparation of the starting materials of the formula X wherein G is hydrogen and $R^1$ is $-SO_2NR_4R_5$. Referring to scheme 4, a compound of formula X wherein $R^1$ is $-SO_2NR^4R^5$ and G is $(C_1-C_3)$alkoxy is reacted with a reducing agent in a reaction inert solvent, for example lithium borohydride ($LiBH_4$) in tetrahydrofuran (THF). The reduction, which yields an alcohol of the formula XVIII, is usually conducted at a temperature from about 0° C. to about 100° C., preferably by heating the reaction mixture to the reflux temperature of the solvent. The alcohol of formula XVIII may then be oxidized using methods known to those skilled in the art. For example, treatment of a solution of such alcohol in a solvent such as methylene chloride with an oxidizing agent such as pyridinium dichromate at a temperature from about 0° C. to about 50° C., preferably at room temperature, will yield the corresponding compounds of formula X wherein G is hydrogen and $R^1$ is $-SO_2NR^4R^5$. Other oxidizing agents/solvent systems such as manganese dioxide/acetone and chromium trioxide/acetic anhydride/acetic acid are also capable of producing this conversion.

The preparation of other compounds of the formula I not specifically described in the foregoing experimental section can be accomplished using combinations of the reactions described above that will be apparent to those skilled in the art.

In each of the reactions discussed or illustrated in schemes 1 to 4 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of the formula I which are also acidic in nature, e.g., where $R^6$ or $R^{10}$ is carboxyphenyl, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of formula I and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the formula I and their pharmaceutically acceptable salts ("the therapeutic compounds") may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueousmedia and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the therapeutic compounds of the present invention as substance P receptor antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radio-labelled substance P ligands at their receptor sites in said isolated cow tissues, thereby affording characteristic $IC_{50}$ values for each compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 4 μg/ml of bacitracin, 4μg/ml of leupeptin, 2μg of chymostatin and 200 g/ml of bovine serum albumin. This step completes the production of the tissue preparation.

The radioligand binding procedure is then carried out in the following manner, viz., by initiating the reaction via the addition of 100 μl of the test compound made up to a concentration of 1 μM, followed by the addition of 100 μl of radioactive ligand made up to a final concentration 0.5 mM and then finally by the addition of 800 μl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The ability of the therapeutic compounds of this invention to inhibit substance P induced effects in vivo may be determined by the following procedures "a" through "d". (Procedures "a" through "c" are described in Nagahisa et al., *European Journal of Pharmacology*, 217, 191–5 (1992), which is incorporated herein by reference in its entirety.)

a. Plasma extravasation in the skin

Plasma extravasation is induced by intradermal administration of substance P (50 μl, 0.01% BSA-saline solution) in dorsal skin of pentobarbital (25 mg/kg i.p.) anesthetized male Hartley guinea pigs weighing 450–500 g. The compound to be tested is dissolved in 0.1% methyl cellulose-water (MC) and dosed p.o. 1 hour before substance P challenge (3 pmol/site). Evans blue dye (30 mg/kg) is administered intravenously 5 minutes before challenge. After 10 minutes, the animals are sacrificed, the dorsal skin is removed, and the blue spots are punched out using a cork borer (11.5 mm oral dose (o.d.)). Tissue dye content is quantitated after overnight formamide extraction at 600 nm absorbance.

b. Capsaicin-induced plasma extravasation

Plasma extravasation is induced by intraperitoneal injection of capsaicin (10 ml of 30 μM solution in 0.1% BSA/saline) into pentobarbital anesthetized (25 mg/kg i.p.) guinea pigs. The compound to be tested is dissolved in 0.1% MC and dosed p.o. 1 hour before capsaicin challenge. Evans blue dye (30 mg/kg) is administered i.v. 5 minutes before challenge. After 10 minutes, the animals are sacrificed, and both right and left ureters are removed. Tissue dye content is quantitated as in "a" above.

c. Acetic acid-induced abdominal stretching

Male ddY mice (SLC, Japan), weighing 14–18 g, were fasted overnight. The compound to be tested is dissolved in 0.1% MC and dosed p.o. 0.5 hour before acetic acid (AA) injection (0.7%, 0.16 ml/10 g body weight). The animals are placed in clear beakers (1 per beaker) and the stretching response is counted 10 to 20 minutes after the AA injection (10 minute interval).

d. Substance p-induced hyperlocomotor paradigm

The anti-psychotic activity of the therapeutic compounds of the present invention as neuroleptic agents for the control of various psychotic disorders may be determined by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

PREPARATION 1

2-Cyclopentyloxy-5-(N-methyl-N-methanesulfonylamino)-benzaldehyde

A. 4-Cyclopentyloxy-N-methanesulfonylaniline

Under $N_2$ in a flame-dried flask, a mixture of 4-cyclopentyloxyaniline (1.0 g, 5.64 mmol) in 25 mL of dry $CH_2Cl_2$ was treated with triethylamine (1.3 mL, 9.38 mmol) and cooled to 0° C. A solution of recrystallized methanesulfonic anhydride (1.5 g, 8.62 mmol) in 10 mL of dry $CH_2Cl_2$ was added dropwise and the reaction was stirred for 1.5 hours. The reaction mixture was then poured into 100 mL of saturated aqueous $NaHCO_3$ and extracted with $CH_2Cl_2$ (3×50 mL). The combined organics were dried over $MgSO_4$, evaporated in vacuo to a dark grey solid and flash chromatographed on silica gel, eluting with hexanes:EtOAc (80:20), to produce the pure intermediate compound, 0.8 g (56%), m.p. 140°–142° C.

B. 4-Cyclopentyloxy-N-methyl-N-methanesulfonylaniline

Under $N_2$ in a flame-dried flask, the preceding intermediate (0.5 g, 1.96 mmol) in 25 mL of acetone was treated with $K_2CO_3$ (0.54 g, 3.91 mmol), stirred for 5 minutes at 25° C. and treated with methyl iodide (0.33 g, 2.32 mmol). After 18 hours, the suspension was filtered through a pad of diatomaeous earth (d.e.), concentrated in vacuo, redissolved in 100 mL of ethyl acetate (EtOAc), refiltered and concentrated to an off-white solid, 300 mg (57%), m.p. 120°–122° C.

C. 2-Cyclopentyloxy-5-(N-methyl-N-methanesulfonylamino)benzaldehyde

Under $N_2$ in a flame-dried flask, the above intermediate from part "B" (300 mg, 1.11 mmol) in 15 mL of $CH_2Cl_2$ was cooled to 0° C. and treated with titanium tetrachloride (0.46 g, 0.27 mL, 2.42 mmol). After 20 minutes at 0° C. α,α-dichloromethyl methyl ether (0.15 g, 0.12 mL, 1.33 mmol) was added and the reaction was left to slowly warm to room temperature overnight. The reaction was quenched in 100 mL of saturated aqueous $NaHCO_3$, extraced with $CH_2Cl_2$ (3×75 mL) and dried over $MgSO_4$. Concentration in vacuo gave a light brown solid which was filtered through a pad of d.e. to obtain the purified title aldehyde, 155 mg (47%).

Mass Spectrum (MS): m/e 297 (p+), 229, 150 (100%).

$^1$H NMR ($CDCl_3$) δ1.6–2.05 (m, 10H), 2.85 (s, 3H), 3.3 (s, 3H), 4.95 (m, 1H), 7.0 (d, 1H), 7.2–7.75 (m, 3H), 10.5 (s, 1H).

The following intermediate aldehydes of the general formula X were prepared by a procedure similar to that of Preparation 1.

2-Methoxy-5-(trifluoromethylthio)benzaldehyde, m.p. 61°–64° C., 30% yield.

5-Tert-butyl-2-methylthiobenzaldehyde, oil, 54% yield, MS: m/e 208 (p+), 193 (100%), 165, 117.

$^1$H NMR ($CDCl_3$) δ1.30 (s, 9H), 2.45 (s, 3H), 7.28 (d, 1H), 7.55 (dd, 1H), 7.82 (d, 1H), 10.3 (s, 1H).

5-Chloro-2-methylthiobenzaldehyde, m.p. 51°–54° C., 52% yield.

2-Methoxy-5-(N-methyl-N-methanesulfonylamino)-benzaldehyde, 89%, $^1$H NMR ($CDCl_3$) δ2.9 (s, 3H), 3.4 (s, 3H), 4.0 (s, 3H), 7.1 (d, 1H), 7.7–7.85 (m, 2H), 10.5 (s, 1H).

2-Methoxy-5-(N-isopropyl-N-methanesulfonylamino)-benzaldehyde, m.p. 114°–116° C., 81% yield.

2-Methoxy-5-(1,1-dioxo-2-thiazolidinyl)benzaldehyde, m.p. 99°–101° C., 82% yield.

2-Isopropoxy-5-(N-methyl-N-methanesulfonylamino)-benzaldehyde, m.p. 107°–110° C., 60% yield.

2-Isopropoxy-5-(N-methyl-N-trifluoromethanesulfonylamino)benzaldehyde, m.p. 42°–45° C., 83% yield.

2-Methoxy-5-(N-methyl-N-trifluoromethanesulfonylamino)-benzaldehyde, 55% yield, $^1$H NMR ($CDCl_3$) δ3.46 (s, 3H), 3.98 (s, 3H), 7.04 (d, 1H), 7.57 (dd, 1H), 7.81 (d, 1H), 10.4 (s, 1H). MS: m/e 297 (p+).

2-Methoxy-5-(N-methyl-N-isopropylsulfonylamino)-benzaldehyde, 39% yield.

2-Methoxy-5-(N-methyl-N-(4-methylphenylsulfonyl)amino)-benzaldehyde, oil, 88% yield.

2-Isopropoxy-5-(N-methyl-N-(4-methylphenylsulfonyl)amino)benzaldehyde, 28% yield, $^1$H NMR ($CDCl_3$) δ1.45 (d, 6H0, 2.42 (s, 3H), 3.10 (s, 3H), 4.70 (m, 1H), 7.0 (m, 3H), 7.25 (m, 3H), 7.42 (d, 2H), 7.58 (dd, 1H), 10.4 (s, 1H). MS: m/e 347 (p+), 305, 150 (100%).

2-Methoxy-5-(N-methyl-N-benzylsulfonylamino)benzaldehyde, 51% yield, $^1$H NMR ($CDCl_3$) δ3.14 (s, 3H), 3.94 (s, 3H), 4.27 (s, 2H), 6.95 (d, 1H), 7.35–7.58 (m, 7H), 10.4 (s, 1H). MS: m/e 319 (p+), 255, 164, 91 (100%).

5-Methoxy-1-methanesulfonyl-2,3-dihydroindol-6-carboxaldehyde, 49% yield, $^1$H NMR ($CDCl_3$) δ2.85 (s, 3H), 3.19 (t, 2H), 3.90 (s, 3H), 3.98 (t, 2H), 6.90 (s, 1H), 7.73 (s, 1H), 10.3 (s, 1H).

5-Methoxy-3-methyl-1-methanesulfonyl-2,3-dihydroindol-6-carboxaldehyde, m.p. 147°–150° C., 49% yield, $^1$H NMR ($CDCl_3$) δ1.45 (d, 3H), 2.75 (dd, 1H), 2.85 (s, 3H), 3.5 (dd, 1H), 3.95 (s, 3H), 4.5 (m, 1H), 6.9 (s, 1H), 7.8 (s, 1H), 10.4 (S,1H).

2-Methoxy-5-(N-cyclopentyl-N-(4-methanesulfonylamino)-benzaldehyde, m.p. 95°–98° C., 62% yield.

2-Methoxy-5-(2-methyl-4-thiazolyl)benzaldehyde, 56% yield, $^1$H NMR ($CDCl_3$) δ2.72 (s, 3H), 3.95 (s, 3H), 7.05 (d, 1H), 7.25 (s, 1H), 8.15 (dd, 1H), 8.25 (d, 1H), 10.5 (s, 1H).

2-Methoxy-5-(N-(3,4-dichlorobenzyl)-N-methanesulfonyl-amino)benzaldehyde, gum, 86% yield, $^1$H NMR ($CDCl_3$) δ2.97 (s, 3H), 3.95 (s, 3H), 4.75 (s, 2H), 6.95 (d, 1H), 7.10 (d, 1H), 7.35 (m, 3H), 7.77 (d, 1H), 10.4 (s, 1H).

2-Methoxy-5-(N-cyclohexylmethyl-N-methanesulfonyl-amino)benzaldehyde, oil, 73% yield, $^1$H NMR ($CDCl_3$) δ0.9–1.8 (m, 11H), 2.85 (s, 3H), 3.48 (d, 2H), 3.98 (s, 3H), 7.05 (d, 1H), 7.60 (dd, 1H), 7.75 (d, 1H), 10.5 (s, 1H).

5-(Isopropylsulfonyl)-2-methoxybenzaldehyde, m.p. 105°–107° C., 57% yield, MS: m/e 242 (M+, 27%), 200 (78%), 136 (100%), $^1$H NMR ($CDCl_3$) δ1.3 (d, 6H), 3.15 (m, 1H), 4.05 (s, 3H), 7.15 (d, 1H), 8.05 (dd, 1H), 8.3 (d, 1H), 10.5 (s, 1H).

5-(N-cyclopentyl-N-methanesulfonyl)amino-2-methoxybenzaldehyde, m.p. 95°–98° C., 62% yield, MS: m/e 297 (M+, 20%), 229, 218 (100%), 150 (95%), $^1$H NMR ($CDCl_3$) δ1.25–1.6 (m, 6H), 1.95 (m, 2H), 2.95 (s, 3H), 3.95 (s, 3H), 4.5 (m, 1H), 7.05 (d, 1H), 7.5 (dd, 1H), 7.7 (d, 1H), 10.45 (s, 1).

5-(N-cyclohexylmethyl-N-methanesulfonyl)amino-2-methoxybenzaldehyde, oil, 74% yield, $^1$H NMR ($CDCl_3$) δ0.9–1.8 (m, 11H), 2.85 (s, 3H), 3.45 (d, 2H), 4.0 (s, 3H), 7.05 (d, 1H), 7.65 (dd, 1H), 7.75 (d, 1H), 10.45 (s, 1H).

2,3-Dihydro-N-methanesulfonyl-5-methoxy-2-methylindole-6-carboxaldehyde, m.p. 147°–150° C., 48% yield, $^1$H NMR ($CDCl_3$) δ1.45 (d, 3H), 2.75 (m, 1H), 2.85 (s, 3H), 3.5 (dd, 1H), 3.9 (s, 3H), 4.5 (m, 1H), 6.9 (s, 1H), 7.83 (s, 1H), 10.4 (s, 1H).

2-Methoxy-5-(N-methyl-N-(2,4-dimethyl-5-thiazolesulfonyl))aminobenzaldehyde, oil, 29% yield, MS: m/e 340 (M+, 10%), 164 (100%), $^1$H NMR ($CDCl_3$) δ2.1 (s, 3H), 2.5 (s, 3H), 3.1 (s, 3H), 3.9 (s, 3H), 7.0 (d, 1H), 7.5 (m, 1H), 7.6 (q, 1H), 10.4 (s, 1H).

2-Methoxy-5-(N-(4,5-dimethyl-2-thiazolyl)-N-methanesulfonyl)aminobenzaldehyde, waxy solid, 39% yield, MS: m/e (340 (M$^+$, 20%), 261 (65%), $^1$H NMR (CDCl$_3$) δ2.3 (d, 6H), 3.4 (s, 3H), 4.0 (s, 3H), 7.0 (s, 3H), 7.0 (d, 1H), 7.7 (q, 1H), 10.5 (s, 1H).

2-Methoxy-5-(N-(4,5-dimethyl-2-thiazolyl)-N-methyl) aminobenzaldehyde, oil, 7% yield, MS: m/e 277 (M$^{+1}$, 20%), 276 (100%), 126 (30), $^1$H NMR (CDCl$_3$) δ2.1 (d, 6H), 3.4 (s, 3H), 4.0 (s, 3H), 7.0 (d, 1H), 7.6 (q, 1H), 7.8 (d, 1H), 10.5 (s, 1H).

2-Methoxy-5-(N-(4,5-dimethyl-2-thiazolyl)) aminobenzaldehyde, m.p. 137°–139° C., 20% yield, MS: m/e 262 (M$^+$, 100%), $^1$H NMR (CDCl$_3$) δ2.15 (s, 3H), 2.25 (s, 3H), 3.9 (s, 3H), 7.0 (d, 1H), 7.6 (dd, 1H), 7.7 (dd, 1H), 10.5 (s, 1H).

2-Methoxy-5-(N-(ethoxycarbonylmethanesulfonyl)-N-methyl)aminobenzaldehyde, oil, 81% yield, $^1$H NMR (CDCl$_3$) δ1.3 (t, 3H), 2.05 (s, 2H), 3.35 (s, 3H), 3.9 (s, 3H), 4.25 (q, 2H), 7.05 (d, 1H), 7.7 (dd, 1H), 7.9 (d, 1H), 10.5 (s, 1H).

2-Methoxy-5-(N-(3,4-dichlorobenzyl)-N-methanesulfonyl)aminobenzaldehyde, 86% yield, $^1$H NMR (CDCl$_3$) δ3.0 (s, 3H), 3.95 (s, 3H), 4.8 (s, 2H), 6.95 (d, 1H), 7.15 (dd, 1H), 7.35 (m, 3H), 7.75 (d, 1H), 10.4 (s, 1H).

PREPARATION 2

2-Methoxy-5-methylthiobenzaldehyde

Under N$_2$ in a flame-dried flask, fitted with a condensor and stirrer, was placed a solution of 1-methoxy-4-methylthiobenzene (2.0 g, 13 mmol) in 75 mL of trifluoroacetic acid (TFA). Hexamethylenetetramine (1.2 g, 13 mmol) was added while stirring the reaction at 25° C. After heating for 2 hours to reflux, the reaction was cooled and concentrated in vacuo and the residue was partitioned between CH$_2$Cl$_2$ and 2N sodium hydroxide (NaOH). The organic layer was dried over MgSO$_4$, concentrated in vacuo to a yellow oil and flash chromatographed on silica gel eluting with hexanes:EtOAc (85:15) to give the pure title compound as a yellow oil, 0.99 g, 42% yield. $^1$H NMR (CDCl$_3$) δ2.5 (s, 3H), 3.95 (s, 3H), 6.97 (d, 1H), 7.5 (dd, 1H), 7.78 (d, 1H), 10.5 (s, 1H).

Using a procedure similar to that of Preparation 2,4-methoxyphenyl cyclohexyl sulfide was converted to 2-methoxy-5-(cyclohexylthio)benzaldehyde, oil. $^1$H NMR (CDCl$_3$) δ1.1–2.0 (m, 10H), 3.0 (m, 1H), 3.95 (s, 3H), 6.95 (d, 1H), 7.62 (dd, 1H), 7.90 (d, 1H), 10.45 (s, 1H).

PREPARATION 3

2-Phenoxybenzaldehyde

A mixture of 2-phenoxybenzyl alcohol (4.0 g, 20.2 mmol, prepared by the reduction of commercially available 2-phenoxybenzoic acid with LiAlH$_4$/THF) and 150 mL CH$_2$Cl$_2$ was treated with pyridinium dichromate (11.39 g, 30.3 mmol) at 25° C. and stirred for another 36 hours. The mixture was filtered through d.e. and then through a pad of silica gel to produce 3.11 g (78%) of title compound as a yellow oil. $^1$H NMR (CDCl$_3$) δ6.8 (d, 1H), 6.9 (d, 1H), 7.0 (m, 2H), 7.1 (m, 2H), 7.2 (m, 1H), 8.9 (m, 1H), 10.2 (s, 1H).

Using a procedure similar to that of Preparation 3, the following benzaldehydes of formula X were prepared from the corresponding compounds of formula XVIII:

5-Diethylaminosulfonyl-2-methoxybenzaldehyde, 76%, $^1$H NMR (CDCl$_3$) δ1.1 (t, 6H), 3.2 (q, 4H), 4.0 (s, 3H), 7.1 (d, 1H), 7.9 (dd, 1H), 8.2 (d, 1H), 10.4 (s, 1H).

5-Diethylaminosulfonyl-2-isopropoxybenzaldehyde, oil, 36%, $^1$H NMR (CDCl$_3$) δ1.2 (t, 6H), 1.4 (d, 6H), 3.2 (q, 4H), 4.8 (m, 1H), 7.1 (d, 1H), 8.0 (dd, 1H), 8.2 (d, 1H), 10.4 (s, 1H).

PREPARATION 4

2-Trifluoromethoxy-5-(N-methyl-N-methanesulfonyl)benzaldehyde

A. To a mixture of concentrated sulfuric acid (81 mL) and concentrated nitric acid (15.5 mL), cooled to 0° C., was added 2-trifluoromethoxybenzaldehyde (25 g, 0.13 mol) portionwise while maintaining the temperature of the reaction below 0° C. After 1.5 hours, the reaction mixture was poured cautiously over 1000 mL of ice in a large beaker and left to stand for 0.5 hours. The resulting suspension was filtered, washed well with H$_2$O and air dried to give crude 5-nitro-2-trifluoromethoxybenzaldehyde, m.p. 32°–34° C.

B. The preceding compound and ethylene glycol (35 mL, 0.62 mol) in 1000 mL of toluene was treated with paratoluenesulfonic acid (0.72 g, 4 mmol) and heated to reflux under N$_2$ for 24 hours, using a Dean-Stark trap to collect the water formed. The solvent was then removed in vacuo and the residue was dissolved in CH$_2$Cl$_2$, washed with saturated aqueous NaHCO$_3$ and dried over MgSO$_4$. Removal of the solvent in vacuo gave crude 2-(5-nitro-2-trifluoromethoxyphenyl)-1,3-dioxolane as a pale orange oil.

C. The dioxolane from part B (5.09 g) in 100 mL of EtOAc was hydrogenated with 0.29 g of 5% palladium on carbon at 45 p.s.i. for 18 hours. After filtration through d.e., the solvent was removed in vacuo to give 2-(5-amino-2-trifluoromethoxyphenyl)-1,3-dioxolane as an orange oil, 4.6 g.

D. The above oil from part C and triethylamine (2.53 mL, 39 mmol) in 200 mL of dry THF was treated with methanesulfonic anhydride (4.9 g, 28 mmol) in 26 mL of THF at 25° C. After 72 hours, 200 mL of H$_2$O was added and the mixture was stirred for another 30 minutes. The aqueous layer was extracted with CH$_2$Cl$_2$ and the organics were combined, washed with 1N HCl, 2N NaOH and H$_2$O, and finally dried over MgSO$_4$. Removal of the solvent in vacuo gave an orange oil which was flash chromatographed on silica gel using hexanes:EtOAc (40:60). Pure 2-(5-methanesulfonylamino-2-trifluoromethoxyphenyl)-1,3-dioxolane was obtained as an oil, 1.64 g.

E. A suspension of sodium hydride (60% oil dispersion, 0.19 g, 4.75 mmol) in 10 mL of dry DMF was treated with the compound from part D (1.5 g, 4.58 mmol) in 20 mL of dry DMF and stirred at 25° C. for 30 minutes. Methyl iodide (0.28 mL, 4.5 mmol) was added and the mixture was stirred for an additional 15 hours. After dilution with 100 mL of water, the mixture was extracted with Et$_2$O (3×100 mL) and the combined organics were dried over MgSO$_4$ and evaporated to give 2-(5-N-methyl-N-methanesulfonylamino)-2-trifluoromethoxyphenyl)-1,3-dioxolane as an orange oil, 1.63 g.

F. The preceding dioxolane from part E (1.63 g) in 30 mL of acetone was treated with 6N HCl at 25° C. for 72 hours. The acetone was then evaporated and the resulting solution was extracted with Et$_2$O and the organics were washed with H$_2$O, dried over MgSO$_4$ and concentrated to an oil. Flash chromatography on silica gel using hexanes:EtOAc (65:35) gave pure 5-(N-methyl-N-methanesulfonylamino)-2-trifluoromethoxy-benzaldehyde as an oil, 0.63 g (42%). $^1$H NMR (CDCl$_3$) δ2.9 (s, 3H), 3.4 (s, 3H), 7.4 (dd, 1H), 7.8 (dd, 1H), 7.9 (d, 1H), 10.4 (s, 1H). MS: m/e 297 (p+), 218, 162.

PREPARATION 5

2-Methoxy-5-methanesulfonylbenzaldehyde

Under $N_2$ in a round-bottomed flask fitted with a condensor, 2-methoxy-5-methylthiobenzaldehyde (0.89 g, 4.9 mmol) was added to 0.6 mL of EtOH. To this, a solution of monoperoxyphthalic acid magnesium salt hexahydrate (2.41 g, 4.9 mmol) in 10.4 mL of $H_2O$ was added and the mixture was heated at 95° C. for 18 hours. The reaction was then quenched with 10 mL of $H_2O$, extracted with $CH_2Cl_2$ (4×10 mL) and the combined organics were dried over $MgSO_4$ and concentrated in vacuo to an oil, 0.34 g. Flash chromatography on silica gel, eluting with EtOAc:hexanes (2.98) gave the pure title compound as a white solid, 0.36 g, m.p. 140°–143° C. $^1H$ NMR (CDCl$_3$) δ3.05 (s, 3H), 4.05 (s, 3H), 7.2 (d, 1H), 8.15 (dd, 1H), 8.40 (d, 1H), 10.5 (s, 1H).

EXAMPLE 1

Cis-3-(5-fluoro-2methylthiobenzyl)amino-2-phenylpiperidine dihydrochloride

A. 5-Fluoro-2-methylthiobenzaldehyde

Under $N_2$ a solution of 8.81 g (62 mmole) of p-fluorothioanisole in 50 mL of dichloromethane was stirred, cooled to 0° C. and treated dropwise with 15 mL (136 mmole) of titanium tetrachloride (TiCl$_4$). After stirring approximately 30 minutes at this temperature, the red solution was treated with 6.73 mL (74.4 mmole) of a α,α-dichloromethyl methyl ether (Aldrich Chem Co.), stirred an additional 2 hours at 0° C. and allowed to warm to room temperature while stirring for another 18 hours. After pouring the reaction mixture into a mixture of 250 mL of saturated aqueous sodium bicarbonate and 250 mL of dichloromethane, the aqueous layer was extracted with three 50 mL portions of dichloromethane and the organic layers were combined and dried over magnesium sulfate (MgSO$_4$). Evaporation of the solvent produced a solid which was recrystallized from hexane; 0.72 g, M.P. 45°–47° C. Mass spectrum (m/e, %); 172 (17), 171 (33), 170 (100, M+), 155 (49), 142 (53), 127 (28).

B. Cis-3-(5-fluoro-2-methylthiobenzyl)amino-6-oxo-2-phenylpiperidine

A mixture of 0.67 g (3.52 mmole) of cis-3-amino-6-oxo-2-phenylpiperidine, 0.72 g (4.23 mmole) of the above aldehyde and 1 g of 3A molecular sieves (Aldrich) in 15 mL of acetic acid was stirred at 25° C. for approximately 1.5 hours, then treated with 1.71 g (8.1 mmole) of sodium triacetoxyborohydride. After stirring for another 18 hours, the mixture was filtered and the filtrate concentrated to a yellow oil. Chromatography on silica gel using dichoromethane:ethanol:concentrated ammonium hydroxide (98:1:1) produced the pure product as an oil which crystallized on standing; 0.51 g (42%), M.P. 125°–130° C. Mass spectrum (m/e, %): 345 (45, M$^{+1}$) 344 (100 M$^+$), 210 (92), 155 (91), 106 (99).

C. Cis-3-(5-fluoro-2-methylthiobenzyl)amino-2-phenylpiperidine dihydrochloride

In a flame-dried flask 0.69 g (2 mmole) of the previous compound in 5 mL of tetrahydrofuran was treated with 3.0 mL of 1.0M borane-tetrahydrofuran complex (Aldrich), refluxed for 1 hour and stirred at 25° C. for 18 hours. After acidifying the crude mixture with 2N hydrochloric acid (HCl), it was extracted with dichloromethane and the aqueous layer was made basic with 2N sodium hydroxide (NaOH). This alkaline layer was finally extracted with dichloromethane which was dried over (MgSO$_4$) and concentrated to an oil; on standing it crystallized to an off-white solid, mp 60°–64° C. This free base was redissolved in dichloromethane and treated with hydrogen chloride (HCl) gas to form the dihydrochloride salt, recrystallized from methanol:diethyl ether as a white crystalline solid, M.P. 270°–273° C. Mass spectrum (m/e, %): 330 (15, M$^+$), 211 (100), 210 (65), 155 (98).

Anal. calc'd for $C_{19}H_{23}FN_2S.0.5\ H_2O$: C, 55.34; H, 6.35; N, 6.79. Found: C, 55.08; H, 6.51; N, 6.59.

The title compounds of Examples 2–8 were prepared by a procedure similar to that of Example 1.

EXAMPLE 2

Cis-3-2-methlthiophenyl)methylamino-2-phenylpiperidine dihydrochloride

M.P. 256°–259° C. (MeOH:Et$_2$O)

MS (m/e, %): 312 (M$^+$), 193, 192, 175, 160, 137 (100)

Anal. calc'd for $C_{19}H_{24}N_2S.2HCl$: C, 59.21; H, 6.80; N, 7.27. Found: C, 59.08; H, 6.92; N, 7.18

EXAMPLE 3

Cis-3-(5-tert-butyl-2-methylthiophenyl)methylamino-2-phenylpiperidine dihydrochloride M.P. 237°–240° C. (MeOH:Et$_2$O)

MS (m/e, %): 368 (3, M$^+$), 367, 264, 210, 175, 155.

Anal. calc'd for $C_{23}H_{32}N_2S.2HCl.0.5\ CH_2Cl_2$: C, 59.65; H, 7.44; N, 6.79. Found: C, 59.37; H, 7.38; N, 6.12.

EXAMPLE 4

Cis-3-(5-chloro-2-methylthiophenyl)methylamino-2-phenylpiperidine dihydrochloride M.P. 260°–265° C. (MeOH:Et$_2$O)

MS (m/e, %): 348, 346 (M$^+$), 227, 180, 171, 120, 106.

Anal. calc'd for $C_{19}H_{23}ClN_2S.2HCl$: C, 54.35; H, 6.00; N, 6.67. Found: C, 54.04; H, 6.08; N, 6.66.

EXAMPLE 5

Cis-3-(2-tert-butylthiophenyl)methylamino-2-phenylpiperidine dihydrochloride M.P. 243°–245° C. dec. (MeOH:Et$_2$O)

MS (m/e, %): 354 (6, M$^+$), 297, 235, 234, 178, 160, 123, 70(100).

Anal. calc'd for $C_{22}H_{30}N_2S.2HCl$: C, 61.81; H, 7.55; N, 6.55. Found: C, 61.46; H, 7.26; N, 6.52.

EXAMPLE 6

Cis-3-(2-(4-chlorophenylthio(phenylmethylamino-2-phenylpiperidine dihydrochloride M.P. 245°–249° C. dec. (MeOH:Et$_2$O)

MS (m/e, %): 408 (M$^+$), 289, 231, 197 (100), 165, 146, 120.

Anal. calc'd for $C_{24}H_{25}ClN_2S.2HCl.1/3\ H_2O$: C, 59.08; H, 5.72; N, 5.74. Found: C, 59.08; H, 5.61; N, 5.84.

EXAMPLE 7

Cis-3-(2-methoxy5-(trifluoromethylthio)phenyl)methylamino-2-phenylpiperidine dihydrochloride M.P. 257°–259° C. (MeOH:Et$_2$O)

Anal. calc'd for $C_{20}H_{23}F_3N_2OS \cdot 2HCl \cdot 1/2H_2O$: C, 50.21; H, 5.48; N, 5.86. Found: C, 50.60; H, 5.42; N, 6.09.

EXAMPLE 8

Cis-3-(2-phenoxyphenyl)methylamino-2-phenylpiperidine hydrochloride

M.P. 210°–212° C. (MeOH:Et$_2$O)

MS (m/e, %): 358 (M$^+$), 239, 198, 183 (100), 175, 160, 146.

Anal. calc'd for $C_{24}H_{26}N_2O \cdot HCl \cdot 1/4H_2O$: C, 71.97; H, 6.79; N, 6.91. Found: C, 72.16; H, 6.94; N, 7.01.

EXAMPLE 9

(+)-(2S,3S)-3-[2-methoxy-5-(N-isopropyl-N-methane-sulfonylamino)benzyl]amino-2-phenylpiperidine dihydrochloride A. (+)-(2S,3S)-3-Amino-2-phenylpiperidine In a bottle were placed 9 g of 10% palladium-carbon, 180 ml of methanol, 275 ml of ethanol, 6.5 ml of concentrated hydrochloric acid and 9 g of the hydrochloride salt of (2S,3S)-3-(2-methoxybenzylamino)-2-phenylpiperidine. The mixture was shaken under hydrogen (40 p.s.i.) overnight, after which 9 g of additional catalyst were added to the system and the mixture was shaken under hydrogen for 1 day. The mixture was diluted with water (250 mL), filtered through diatomaceous earth (Celite (trademark)) and the Celite was rinsed well with water. The filtrate was concentrated to a volume of ca. 600–700 mL, made basic with concentrated aqueous sodium hydroxide and extracted with chloroform. The chloroform extracts were dried (sodium sulfate) and concentrated to obtain 4.4 g of the title compound as a colorless oil.

$[\alpha]_D$ (HCl salt)=+62.8° (c=0.46, methanol (CH$_3$OH)).

$^1$H NMR (CDCl$_3$) δ1.68 (m, 4H), 2.72 (m, 1H), 2.94 (broad s, 1H), 3.16 (m, 1H), 3.80 (d, 1H, J=3), 7.24 (m, 5H).

HRMS calc'd for $C_{11}H_{16}N_2$: 176.1310. Found: 176.1309.

Anal. calc'd for $C_{11}H_{16}N_2 \cdot 2HCl \cdot 1/3H_2O$: C, 51.78; H, 7.36; N, 10.98. Found: C, 51.46; H, 7.27; N, 10.77.

B. (+)-(2S,3S)-3-[2-methoxy-5-(N-isopropyl-N-methane-sulfonylamino)benzyl]amino-2-phenylpiperidine dihydrochloride Under a nitrogen atmosphere in a round-bottom flask were placed 80 mg (0.46 mmol) of (+)-(2S,3S)-3-amino-2-phenylpiperidine, 5 ml of acetic acid and 150 mg (0.55 mmol) of 2-methoxy-5-(N-isopropyl-N-methanesulfonylamino)benzaldehyde, and the mixture was stirred for 60 minutes. To the system were added 0.21 g (1.0 mmol) of sodium triacetoxyborohydride, and the mixture was stirred at room temperature overnight. The mixture was concentrated, basified with 1M aqueous sodium hydroxide and extracted with methylene chloride. The methylene chloride extracts were washed with water and extracted with 1M aqueous hydrochloric acid. The hydrochloric acid extracts were basified with 1M aqueous sodium hydroxide and extracted with methylene chloride. The methylene chloride extracts were dried (sodium sulfate) and concentrated to obtain 528 mg of colorless oil. The oil was dissolved in methylene chloride, and ether saturated with hydrogen chloride was added to the solution. The resulting white solid was collected by filtration and stirred in isopropanol at 60° C. for 2 hours. Filtration afforded 128 mg of the title compound as its hydrochloride.

M.P. 268°–270° C.

$^1$H NMR (CDCl$_3$; free base) δ1.0 (d, 6H), 1.38–2.20 (m, 6H), 2.80 (m, 2H), 2.85 (s, 3H), 3.2 (t, 1H), 3.35 (d, 1H), 3.50 (s, 3H), 3.70 (d, 1H), 3.90 (d, 1H), 4.50 (m, 1H), 6.65 (d, 1H), 6.90 (d, 1H), 7.05 (dd, 1H), 7.25 (m, 5H).

Mass spectrum: m/z 431 (parent), 312 (100%).

Anal. calc'd for $C_{23}H_{33}N_3O_3S \cdot 2HCl$: C, 54.75; H, 6.99; N, 8.32. Found: C, 54.75; H, 6.99; N, 8.29.

The title compounds of Examples 10–37 were prepared from either (+)-(2S,3S)-3-amino-2-phenylpiperidine or the corresponding racemate by employing the appropriate aldehyde and using a procedure similar to that of Example 9B.

EXAMPLE 10

(2S,3S)-3-(2-Methoxy-5-methylmercaptobenzylamino)-2-phenylpiperidine hydrochloride M.P. 257°–259° C. (dec.)

$^1$H NMR (free base; CDCl$_3$) δ1.32 (m, 1H), 1.50 (m, 1H), 1.82 (m, 1H), 2.04 (m, 1H), 2.30 (s, 3H), 2.72 (m, 2H), 3.18 (m, 1H), 3.26 (d, 1H, J=15), 3.36 (s, 3H), 3.54 (d, 1H, J=15), 3.80 (d, 1H, J=3), 6.52 (d, 1H, J=10), 6.90 (d, 1H, J=3), 7.04 (dd, 1H, J=3, 10), 7.2 (m, 5H).

HRMS calc'd for $C_{20}H_{26}N_2OS$: 342.1760. Found: 342.1770.

Anal. calc'd for $C_{20}H_{26}N_2OS \cdot 2HCl \cdot 0.25H_2O$: C, 57.20; H, 6.84; N, 6.67. Found: C, 57.35; H, 6.76; N, 6.61.

EXAMPLE 11

(2S,3S)-3-(2-Methoxy-5-methylsulfoxybenzylamino)-2-phenylpiperidine hydrochloride M.P. 209° C. (dec).

$^1$H NMR (free base; CDCl$_3$) δ1.40 (m, 1H), 1.56 (m, 1H), 1.90 (m, 1H), 2.10 (m, 1H), 2.59, 2.62 (2S,3H), 2.76 (m, 2H), 3.22 (m, 1H), 3.42 (m, 1H), 3.49, 3.52 (2S,3H), 3.66 (m, 1H), 3.86 (d, 1H, J=3), 6.76 (m, 1H), 7.24 (m, 6H), 7.46 (m, 1H).

HRMS calc'd for $C_{20}H_{27}N_2O_2S$(M+1): 359.1787. Found: 359.1763.

EXAMPLE 12

(2S,3S)-3-(2-Methoxy-5-methylsulfonylbenzylamino)-2-phenylpiperidine hydrochloride

M.P.>260° C.

$^1$H NMR (free base; CDCl$_3$) δ1.40 (m, 1H), 1.58 (m, 1H), 1.88 (m, 1H), 2.10 (m, 1H), 2.78 (m, 2H), 2.96 (s, 3H), 3.24 (m, 1H), 3.38 (d, 1H, J=15), 3.54 (s, 3H), 3.66 (d, 1H, J=15), 3.90 (d, 1H, J=3), 6.74 (d, 1H, J=10), 7.26 (m, 5H), 7.58 (d, 1H, J=3), 7.72 (d, 1H, J=10).

HRMS calc'd for $C_{20}H_{26}N_2O_3S$: 374.1658. Found: 374.1622.

EXAMPLE 13

(2S,3S)-3-(2-Methoxy-5-phenoxybenzylamino)-2-phenylpiperidine hydrochloride

M.P.>250° C.

$^1$H NMR (free base; CDCl$_3$) δ1.34 (m, 1H), 1.74 (m, 2H), 2.06 (m, 1H), 2.76 (m, 2H), 3.22 (m, 1H), 3.32 (d, 1H, J=15), 3.44 (s, 3H), 3.60 (d, 1H, J=15), 3.85 (d, 1H, J=3), 6.60 (d, 1H, J=9), 6.67 (d, 1H, J=3), 6.78 (dd, 1H, J=6,9), 6.86 (d, 2H), 7.00 (t, 1H, J=6), 7.22 (m, 7H).

HRMS calc'd for $C_{25}H_{28}N_2O_2$: 388.2151. Found: 388.2137.

EXAMPLE 14

(2S,3S)-3-(2-Methoxy-5-N-methylmethanesulfonylamino-benzylamino)-2-phenylpiperidine hydrochloride

M.P. 281°–283° C.

$^1$H NMR (free base; CDCl$_3$) δ1.42 (m, 1H), 1.74 (m, 2H), 2.12 (m, 1H), 2.78 (m, 5H), 3.20 (s, 3H), 3.24 (m, 1H), 3.36 (d, 1H, J=15), 3.52 (s, 3H), 3.64 (d, 1H, J=15), 3.89 (d, 1H, J=3), 6.64 (d, 1H, J=9), 6.98 (d, 1H, J=3), 7.14 (dd, 1H, J=3, 9), 7.26 (m, 5H).

HRMS calc'd for $C_{21}H_{29}N_3O_3S$: 403.1992. Found: 403.1923.

Anal. calc'd for $C_{21}H_{29}N_3O_3S.2HCl$. 1/3H$_2$O: C, 52.28; H, 6.61; N, 8.71. Found: C, 52.09; H, 6.63; N, 8.68.

EXAMPLE 15

Cis-3-[2-isopropoxy-5-(N-methyl-N-methanesulfonyl-amino)benzyl]amino-2-phenylpiperidine dihydrochloride M.P. 278°–280° C., 39% yield.

Anal. calc'd for $C_{23}H_{33}N_3O_3S.2HCl$: C, 54.75; H, 6.99; N, 8.32. Found: C, 54.83, H, 7.16, N, 8.16.

$^1$H NMR (free base, CDCl$_3$) δ1.10 (dd, 6H), 1.15–2.1 (m, 6H), 2.65–2.90 (m+s, 5H), 3.05–3.25 (m+s, 4H), 3.35 (d, 1H), 3.55 (d, 1H), 3.90 (d, 1H), 4.30 (m, 1H), 6.65 (d, 1H), 6.95 (d, 1H), 7.05–7.4 (m, 6H).

EXAMPLE 16

Cis-3-[2-methoxy-5-(N-isopropyl-N-methanesulfonyl-amino)benzyl]amino-2-phenylpiperidine dihydrochloride M.P. 268°–270° C., 65% yield.

Anal. calc'd for $C_{23}H_{33}N_3O_3S.2HCl$: C, 54.75; H, 6.99; N, 8.32. Found: C, 54.75, H, 6.99, N, 8.29.

$^1$H NMR (free base, CDCl$_3$) δ1.10 (dd, 6H), 1.45 (d, 1H), 1.60 (tt, 1H), 1.7–1.95 (m, 3H), 2.12 (d, 1H), 2.80 (m, 2H), 2.90 (s, 3H), 3.25 (d, 1H), 3.35 (d, 1H), 3.50 (s, 3H), 3.70 (d, 1H), 3.90 (d, 1H), 4.50 (m, 1H), 6.65 (d, 1H), 6.90 (d, 1H), 7.05 (dd, 1H), 7.30 (m, 5H).

EXAMPLE 17

Cis-3-[2-methoxy-5-(N-methyl-N-trifluoromethane-sulfonylamino)benzyl]amino-2-phenylpiperidine dihydrochloride M.P. 245°–250° C., 24% yield.

Anal. calc'd for $C_{21}H_{26}F_3N_3O_3S.2HCl$: C, 47.55; H, 5.32; N, 7.92. Found: C, 47.55, H, 5.32, N, 7.86.

$^1$H NMR (free base, CDCl$_3$) δ1.50 (d, 1H), 1.60 (tt, 1H), 1.8–2.00 (m, 3H), 2.15 (d, 1H), 2.85 (m, 2H), 3.25 (d, 1H), 3.35 (s, 3H), 3.40 (d, 1H), 3.50 (s, 3H), 3.65 (d, 1H), 3.90 (d, 1H), 6.65 (d, 1H), 6.98 (d, 1H), 7.10 (dd, 1H), 7.25 (m, 5H).

EXAMPLE 18

Cis-3-[2-methoxy-5-(N-thiazolidine-S,S-dioxide)-benzyl]amino-2-phenylpiperidine dihydrochloride M.P. 263°–265° C., 36% yield.

Anal. calc'd for $C_{22}H_{29}N_3O_3S.2HCl$: C, 54.09; H, 6.40; N, 8.60. Found: C, 53.87, H, 6.43, N, 8.45.

$^1$H NMR (free base, CDCl$_3$) δ1.40 (d, 1H), 1.60 (tt, 1H), 1.75 (m, 2H), 1.90 (m, 1H), 2.15 (d, 1H), 2.50 (m, 2H), 2.80 (m, 2H), 3.2–3.50 (m, 7H), 3.55–3.70 (m, 3H), 3.90 (d, 1H), 6.65 (d, 1H), 6.95 (d, 1H), 7.1–7.40 (m, 6H).

EXAMPLE 19

Cis-3-[2-trifluoromethoxy-5-(N,N-bis(methanesulfonyl)-amino)benzyl]amino-2-phenylpiperidine dihydrochloride M.P. 256°–257° C., 29% yield.

Anal. calc'd for $C_{21}H_{26}F_3N_3O_5S_2.2HCl$: C, 42.43; H, 4.75; N, 7.07. Found: C, 42.38, H, 4.77, N, 6.94.

$^1$H NMR (free base, CDCl$_3$) δ1.50 (d, 1H), 1.6–1.90 (m, 4H), 2.10 (d, 1H), 2.75–2.95 (m, 2H), 3.2–3.40 (m+s, 7H), 3.50 (d, 1H), 3.65 (d, 1H), 3.95 (d, 1H), 7.15–7.45 (m, 8H).

EXAMPLE 20

Cis-3-[2-methoxy-5-(N,N-diethylaminosulfonyl)-benzyl]amino-2-phenylpiperidine dihydrochloride M.P. 267°–269° C., 29% yield.

Anal. calc'd for $C_{23}H_{33}N_3O_3S_2.2HCl$: C, 54.75; H, 6.99; N, 8.32. Found: C, 54.98; H, 7.34; N, 8.18.

$^1$H NMR (free base, CDCl$_3$) δ1.15 (t, 6H), 1.50 (d, 1H), 1.6–2.00 (m, 4H), 2.10 (d, 1H), 2.80 (m, 2H), 3.15 (q, 4H), 3.30 (d, 1H), 3.55 (s+d, 4H), 3.70 (d, 1H), 3.95 (d, 1H), 6.70 (d, 1H), 7.30 (m, 5H), 7.65 (dd, 1H).

EXAMPLE 21

Cis-3-[2-trifluoromethoxy-5-(N-methyl-N-methane-sulfonylamino)benzyl]amino-2-phenylpiperidine dihydrochloride M.P. 247°–248° C., 43% yield.

Anal. calc'd for $C_{21}H_{26}F_3N_3O_3S_2.2HCl$: C, 47.55; H, 5.32; N, 7.92. Found: C, 47.51, H, 5.47, N, 7.60.

$^1$H NMR (free base, CDCl$_3$) δ1.50 (d, 1H), 1.6–1.95 (m, 4H), 2.10 (d, 1H), 2.75 (s, 3H), 2.85 (m, 2H), 3.15 (s, 3H), 3.30 (d, 1H), 3.50 (d, 1H), 3.65 (d, 1H), 3.95 (d, 1H), 7.1–7.45 (m, 8H).

EXAMPLE 22

Cis-3-[2-isopropoxy-5-(N-methyl-N-trifluoromethane-sulfonylamino)benzyl]amino-2-phenylpiperidine dihydrochloride M.P. 267°–273° C., 7% yield.

Anal. calc'd for $C_{23}H_{30}F_3N_3O_3S_2.2HCl$: C, 49.46; H, 5.41; N, 7.52. Found: C, 49.71, H, 5.72, N, 7.30.

$^1$H NMR (free base, CDCl$_3$) δ1.15 (dd, 6H), 1.4–1.95 (m, 5H), 2.15 (d, 1H), 2.30 (m, 2H), 3.15–3.4 (m+s, 5H), 3.55 (d, 1H), 3.90 (d, 1H), 4.35 (m, 1H), 6.65 (d, 1H), 6.95 (d, 1H), 7.10 (dd, 1H), 7.30 (m, 5H).

EXAMPLE 23

Cis-3-[2-methoxy-5-(N-methyl-N-isopropylsulfonyl-amino)benzyl]amino-2-phenylpiperidine dihydrochloride M.P. 264°–266° C., 22% yield.

Anal. calc'd for $C_{23}H_{33}N_3O_3S.2HCl$: C, 54.75; H, 6.99; N, 8.32. Found: C, 54.91, H, 7.04, N, 8.23.

¹H NMR (free base, CDCl₃, δ) 1.35 (d, 6H), 1.45 (d, 1H), 1.55–1.95 (m, 4H), 2.15 (d, 1H), 2.85 (m, 2H), 3.25 (m+s, 5H), 3.35 (d, 1H), 3.50 (s, 3H), 3.65 (d, 1H), 3.90 (d, 1H), 6.65 (d, 1H), 7.05 (d, 1H), 7.15–7.35 (m, 6H).

EXAMPLE 24

Cis-3-[2-cyclopentyloxy-5-(N-methyl-N-methanesulfonyl-amino)benzyl]amino-2-phenylpiperidine dihydrochloride hemihydrate M.P. 252°–255° C., 37% yield.

Anal. calc'd for C₂₅H₃₅N₃O₃S.2HCl.1/2H₂O: C, 55.65, H, 7.10, N, 7.79. Found: C, 55.51, H, 6.95, N, 7.73.

¹H NMR (free base, CDCl₃) δ1.4–1.95 (m, 13H), 2.10 (d, 1H), 2.7–2.90 (m+s, 5H), 3.20 (s, 3), 3.25 (d, 1H), 3.35 (d, 1H), 3.55 (d, 1H), 3.85 (d, 1H), 4.55 (m, 1H), 6.65 (d, 1H), 6.95 (d, 1H), 7.10 (dd, 1H), 7.25 (m, 5H).

EXAMPLE 25

Cis-3-[2-methoxy-5-(N-methyl-N-(4-methylphenylsulfonyl)amino)benzyl]amino-2-phenylpiperidine dihydrochloride M.P. 215°–220° C., 42% yield.

Anal. calc'd for C₂₇H₃₃N₃O₃S.2HCl: C, 58.69, H, 6.38, N, 7.60. Found: C, 58.46, H, 6.30, N, 7.41. ¹H NMR (free base, CDCl₃, δ) 1.30–2.04 (m, 7H), 2.40 (s, 3H), 2.74 (m, 2H), 3.05 (s, 3H), 3.25 (d, 1H), 3.40 (s, 3H), 3.52 (d, 1H), 3.80 (d, 1H), 6.52 (d, 1H), 6.62 (d, 1H), 6.85 (dd, 1H), 7.10–7.42 (m, 9H).

EXAMPLE 26

Cis-3-[2-isopropoxy-5-(N-methyl-N-(4-methylphenylsulfonyl)amino)benzyl]amino-2-phenylpiperidine dihydrochloride M.P. 215°–219° C., 3.2% yield.

Anal. calc'd for C₂₉H₃₇N₃O₃S.2HCl: C, 59.99, H, 6.77, N, 7.23. Found: C, 59.98, H, 6.83, N, 7.19.

¹H NMR (free base, CDCl₃, δ) 1.04 (dd, 6H), 1.30–2.05 (m, 7H), 2.40 (s, 3H), 2.75 (m, 2H), 3.04 (s, 3H), 3.24 (d, 1H), 3.44 (d, 1H), 3.80 (d, 1H), 4.26 (m, 1H), 6.55 (d, 1H), 6.63 (d, 1H), 6.85 (dd, 1H), 7.10–7.42 (m, 9H).

EXAMPLE 27

Cis-3-[2-isopropoxy-5-(N-isopropyl-N-methanesulfonylamino)benzyl]amino-2-phenylpiperidine dihydrochloride M.P. 243°–246° C., 23% yield.

Anal. calc'd for C₂₅H₃₇N₃O₃S.2HCl: C, 56.38, H, 7.38, N, 7.89. Found: C, 56.52, H, 7.03, N, 7.70.

¹H NMR (free base, CDCl₃, δ) 1.10–1.5 (dd+dd, 12H), 1.40–2.20 (m, 6H), 2.60 (m, 2H), 2.80 (s, 3H), 3.30 (m, 1H), 3.35 (d, 1H), 3.65 (d, 1H), 3.80 (d, 1H), 4.35 (m, 1H), 4.50 (m, 1H), 6.95 (d, 1H), 7.05 (dd, 1H), 7.30 (m, 5H).

EXAMPLE 28

Cis-3-[2-isopropoxy-5-(N,N-diethylaminosulfonyl)-benzyl]amino-2-phenylpiperidine dihydrochloride M.P. 246°–248° C. (dec.), 98% yield.

Anal. calc'd for C₂₅H₃₇N₃O₃S.2HCl: C, 56.39, H, 7.38, N, 7.89. Found: C, 56.29, H, 7.29, N, 7.82.

¹H NMR (free base, CDCl₃, δ) 1.11 (m, 12H), 1.37–2.15 (m, 6H), 2.72–2.83 (m, 2H), 3.12–3.28 (q+m, 5H), 3.33 (d, 1H), 3.60 (d, 1H), 3.85 (d, J=2.2 Hz, 1H), 4.38 (m, 1H), 6.71 (d, 1H), 7.25 (m, 5H), 7.48 (d, 1H), 7.57 (dd, 1H).

EXAMPLE 29

Cis-3-[2-methoxy-5-(N-methyl-N-phenylmethylsulfonylamino)benzyl]amino-2-phenylpiperidine dihydrochloride M.P. 266°–269° C. (dec.), 23% yield.

Anal. calc'd for C₂₇H₃₃N₃O₃S.2HCl: C, 58.69, H, 6.39, N, 7.60. Found: C, 58.70, H, 6.54, N, 7.41.

¹H NMR (free base, CDCl₃, δ) 1.40–2.30 (m, 6H), 2.80 (m, 2H), 3.07 (s, 3H), 3.30 (m, 1H), 3.35 (d, 1H), 3.50 (s, 3H), 3.65 (d, 1H), 3.90 (d, 1H), 4.20 (s, 2H), 6.62 (d, 1H), 6.90 (d, 1H), 7.08 (dd, 1H), 7.20–7.45 (m, 10H).

EXAMPLE 30

Cis-3-[(2,3-dihydro-5-methoxy-1-methanesulfonyl-6-indolyl)methylamino]-2-phenylpiperidine dihydrochloride M.P. 255°–258° C., 27% yield.

Anal. calc'd for C₂₂H₂₉N₃O₃S.2HCl: C, 54.09, H, 6.40, N, 8.60. Found: C 54.10, H, 6.21, N, 8.52.

¹H NMR (free base, CDCl₃, δ) 1.35–2.20 (m, 7H), 2.75 (m, 1H), 2.80 (s, 3H), 3.05 (t, 2H), 3.25 (m, 1H), 3.35 (d, 1H), 3.40 (s, 3H), 3.60 (d, 1H), 3.95 (m, 3H), 6.55 (s, 1H), 7.15 (s, 1H), 7.30 (m, 5H).

EXAMPLE 31

(1SR,2SR,3SR,4RS)-3-(2-methoxy-5-(N-methyl-N-methanesulfonylamino)benzyl)-amino-2-benzhydryl-[2.2.1]-azanorbornane dihydrochloride monohydrate

M.P. 196°–200° C.

Anal. calc'd for C₂₉H₃₅N₃O₃S.2HCl.H₂O: C, 58.38, H, 6.59; N, 7.04. Found: C, 58.71; H, 6.52; N, 6.93.

¹H NMR (D₂O, δ) 1.85 (m, 1H), 2.35 (m, 1H), 3.06 (s, 3H), 3.27–3.63 (m+s+s, 10H), 3.85 (d, 1H), 3.96 (d+d, 2H), 4.26 (d, 1H), 4.39 (d, 1H), 4.8 (s, D₂O), 5.16 (m, 1H), 6.97 (d, 1H), 7.21 (d, 1H), 7.31–7.50 (m, 1H).

EXAMPLE 32

(1SR,2SR,3SR,4RS)-3-(2-isopropoxy-5-(N-methyl-N-methanesulfonylamino)benzyl)amino-2-benzhydryl-[2.2.1]-azanorbornane dihydrochloride monohydrate

M.P. 182°–183° C.

Anal. calc'd for C₃₁H₃₉N₃O₃S.2HCl.H₂O: C, 53.54; H, 5.58; N, 6.46. Found: C, 53.36; H, 5.71; N, 6.40.

1H NMR (D₂O, δ) 1.20 (t, 6H), 1.90 (m, 1H), 2.35 (m, 1H), 3.06 (s, 3H), 3.26 (s, 3H), 3.29–3.47 (m, 4H), 3.84 (m, 3H), 4.14 (d, 1H), 4.36 (d, 1H), 4.45 (m, 1H), 4.80 (s, D₂O), 5.08 (m, 1H), 6.96–7.04 (m, 2H), 7.26–7.47 (m, 11H).

EXAMPLE 33

(1SR,2SR,3SR,4RS)-3-(2-methoxy-5-(N-methyl-N-trifluoromethanesulfonylamino)benzyl)amino-2-benzhydryl-[2.2.1]-azanorbornane dihydrochloride

M.P. 186° C.

HRMS calc'd for $C_{29}H_{32}F_3N_3O_3S$: 559.2116. Found: 559.2197.

$^1$H NMR ($D_2O$, δ) 1.85 (m, 1H), 2.34 (m, 1H), 3.36–3.55 (m+s, 10H), 3.72–3.85 (d+d, 4H), 4.14 (d, 1H), 4.37 (d, 1H), 4.80 (s, $D_2O$), 5.03 (m, 1H), 6.97 (d, 1H), 7.24 (d, 1H), 7.32–7.53 (m, 11H).

EXAMPLE 34

(1SR,2SR,3SR,4RS)-3-(2-methoxy-5-(N-methyl-N-phenylmethanesulfonylamino)benzyl)amino-2-benzhydryl-[2.2.1]-azanorbornane dihydrochloride hydrate

M.P. 178° C.

Anal. calc'd for $C_{35}H_{39}N_3O_3S\cdot 2HCl\cdot 1.5H_2O$: C, 58.76; H, 7.00; N, 6.63. Found: C, 59.15; H, 6.60; N, 6.40.

$^1$H NMR ($D_2O$, δ) 1.81 (m, 1H), 2.32 (m, 1H), 3.24–3.37 (m, 8H), 3.51 (m, 3H), 3.68 (m, 2H), 3.79 (d, 1H), 3.95 (d, 1H), 4.35 (d, 1H), 4.62 (s, 1H), 4.82 (s+m, 1H), 4.97 (m, 1H), 6.69 (d, 1H), 6.85 (d, 1H), 7.11 (dd, 1H), 7.37–7.50 (m, 15).

EXAMPLE 35

(1SR,2SR,3SR,4RS)-3-(2-methoxy-5-(N-isopropyl-N-methanesulfonylamino)benzyl)amino-2-benzhydryl-[2.2.1]-azanorbornane dihydrochloride M.P. 238° C. (dec.).

Anal. calc'd for $C_{31}H_{39}N_3O_3S\cdot 2HCl$: C, 61.08; H, 6.49; N, 6.74; N, 6.74. Found: C, 61.38; H, 6.81; N, 6.93.

$^1$H NMR ($D_2O$, δ) 1.14 (d, 6H), 1.87 (m, 1H), 2.38 (m, 1H), 3.18 (s, 3H), 3.34–3.61 (m+s, 7H), 3.89 (d, 1H), 4.05 (m, 2H), 4.31–4.46 (m, 3H), 4.8 (s, $D_2O$), 5.19 (m, 1H), 7.01 (d, 1H), 7.20 (d, 1H), 7.34–7.52 (m, 11H).

EXAMPLE 36

(1SR,2SR,3SR,4RS)-3-(2-methoxy-5-(1,1-dioxo-2-isothiazolidinyl)benzyl)amino-2-benzhydryl-[2.2.1]-azanorbornane dihydrochloride

M.P. 206°–207° C.

Anal. calc'd for $C_{30}H_{35}N_3O_3S\cdot 2HCl$: C: 60.09; H, 6.39; N, 7.01. Found: C, 59.77; H, 6.15; N, 6.94.

$^1$H NMR ($D_2O$, δ) 1.90 (m, 1H), 2.35 (m, 1H), 2.56 (m, 2H), 3.33–3.62 (m+s, 10H), 3.77–3.83 (m, 4H), 3.96 (d, 1H), 4.15 (d, 1H), 4.41 (d, 1H), 4.8 (s, $D_2O$), 5.10 (m, 1H), 7.00 (d, 1H), 7.13 (d, 1H), 7.32–7.47 (m, 11H).

EXAMPLE 37

(1SR,2SR,3SR,4RS)-3-[(2,3-dihydro-5-methoxy-1-methanesulfonyl-6-indolyl)methylamino)benzyl]-2-benzhydryl[2.2.1]-azanorbornane dihydrochloride

M.P. 250° C.

Anal. calc'd for $C_{30}H_{35}N_3O_3S\cdot 2HCl$: C, 63.34; H, 6.38; N, 6.33. Found: C, 63.48; H, 6.15; N, 6.32.

$^1$H NMR ($D_2O$, δ) 1.90 (m, 1H), 2.38 (m, 1H), 2.99 (s, 3H), 3.20 (t, 2H), 3.33–3.55 (m+s, 8H), 3.86 (d, 1H), 3.97–4.06 (m, 4H), 4.19 (d, 1H), 4.39 (d, 1H), 4.82 (s, $D_2O$), 5.13 (m, 1H), 6.96 (s, 1H), 7.12 (s, 1H), 7.36–7.51 (m, 10H).

EXAMPLE 38

(2S,3S)-N-(2-Methoxy-5-methylthiophenyl)methyl-2-diphenylmethyl-1-azabicyclo[2.2.2]octan-3-amine Mesylate A. (2S,3S)-2-Diphenylmethyl-1-azabicyclo[2.2.2]octan-3-amine (2S,3S)-N-(2-methoxyphenyl)methyl-2-diphenylmethyl-1-azabicyclo[2.2.2]octan-3-amine (4.13 g, 10 mmol) was hydrogenated in methanol (MeOH) (40 ml)/6N HCl (10 ml) by using 20% palladium hydroxide on carbon (0.2 g) at 2.5 kg/cm$^2$ of hydrogen for 60 hours. The filtrate was concentrated and the residue was partitioned between 2N NaOH and $CH_2Cl_2$. The organic layer was dried over $MgSO_4$, and concentrated to give the crude product, which was recrystallized from ethanol (EtOH) to afford the pure title compound (2.80 g, 96%).

B. 2-Methoxy-5-methylthiobenzaldehyde 2-(2-Methoxy-5-methylthiophenyl)-1,3-dioxolane(2.40 g, 10 mmol) was stirred in 1N HCl (2 ml)/acetone (30 ml). After the starting material disappeared (ca. 2 hours), the solution was concentrated. The residue was partitioned between methylene chloride ($CH_2Cl_2$) and saturated sodium bicarbonate ($NaHCO_3$) solution. The organic layer was washed with $H_2O$, dried over $MgSO_4$, and evaporated to give the aldehyde. (1.96 g, 100%).

C. (2S,3S)-N-(2-Methoxy-5-methylthiophenyl)methyl-2-diphenylmethyl-1-azabicyclo[2.2.2]octan-3-amine Mesylate To a solution of a 2-methoxy-5-methylthiobenzaldehyde (765 mg, 4.2 mmol) and (2S,3S)-diphenylmethyl-1-azabicyclo[2.2.2]octan-3-amine (1170 mg, 4 mmol) in $CH_2Cl_2$ (40 ml) was added in portions sodium triacetoxyborohydride (933 mg, 4.4 mmol). The mixture was stirred until the amine disappeared. The solution was carefully neutralized with an ice cooled saturated $NaHCO_3$ solution. The organic layer was washed with $H_2O$, dried over $MgSO_4$, and concentrated to give the product (1.61 g, 88%). To the solution of the product in acetone was added one equivalent methanesulfonic acid. Then the precipitated mesylate salt was collected (1.51 g, 66%).

M.P. 234° C.

IR (KBr) cm$^{-1}$: 3400, 2950, 1630, 1600, 1490, 1455, 1240, 1210, 1195, 1060, 785, 750, 710.

$^1$H NMR ($CDCl_3$) δ: 8.40 (1H, br), 7.5–7.2 (10H, m), 7.17 (1H, d, J=8.4 Hz), 6.69 (1H, d, J=8.4 Hz), 6.66 (1H, br, s), 4.56 (1H, d, J=12.1 Hz), 4.25 (1H, m), 3.70–3.35 (5H, m), 3.55 (3H, s), 3.30–3.15 (2H, m), 2.46 (3H, s), 2.42 (3H, s), 2.25 (1H, m), 2.05 (1H, m), 2.00–1.60 (3H, m).

EXAMPLE 39

(2S,3S)-N-(2-Methoxy-5-methylsulfinylphenyl) methyl-2-diphenylmethyl-1-azabicyclo[2.2.2]octan-3-amine Hydrochloride A solution of (2S,3S)-N-(2-methoxy-5-methylthiophenyl)-methyl-2-diphenylmethyl-1-azabicyclo[2.2.2.]octan-3-amine (180 mg, 0.392 mmol) in MeOH (20 ml) was added to a solution of sodium periodate ($NaIO_4$) (92 mg, 0.432 mmol) in $H_2O$ (10 ml). The mixture was stirred for 24 hours. The precipitate ($NaIO_3$) was filtered off. The filtrate was concentrated and the residue was partitioned between $H_2O$ and $CH_2Cl_2$ (20 ml). The water layer was extracted twice with $CH_2Cl_2$. The combined $CH_2Cl_2$ was dried overd $MgSO_4$ and concentrated to give the sulfoxide, which was converted to HCl salt by using HCl-ether. (Yield, 180 mg, 97%).

M.P. 183° C.

IR (KBr) cm$^{-1}$: 3420, 3190, 1605, 1495, 1455, 1260, 1020, 755, 710.

$^1$H NMR ($CDCl_3$+DMSO) δ: 8.11 (1H, br), 8.00 (1H, br), 7.70 (2H, m), 7.65 (1H, m), 7.44–7.20 (7H, m), 6.92 (1H, m), 6.48 (1H, br), 5.49 (1H, m), 4.45 (1H, br), 4.20 (2H, m), 3.95 (1H, m), 3.16 (1.5H, s), 3.12 (1.5H, s), 3.15 (2H, m), 2.80 (1.5H, s), 2.77 (1.5H, s), 2.85–2.50 (5H, m), 2.15–1.85 (2H, m).

EXAMPLE 40

(2S,3S)-N-(5-Ethylthio-2-methoxyphenyl)methyl-2-diphenylmethyl-1-azabicyclo[2.2.2]octan-3-amine Hydrochloride The title compound was obtained using the same procedure as described in Example 38, except that 5-ethylthio-2-methoxybenzaldehyde was substituted for 2-methoxy-5-methylthiobenzaldehyde. The yield of the product was 76%.

M.P. 254° C.

IR (KBr) cm$^{-1}$: 3450, 3190, 2950, 1490, 1455, 1250, 1030, 715.

$^1$H NMR (DMSO) δ: 7.97 (1H, br), 7.68 (2H, m), 7.51 (2H, m), 7.50–6.85 (9H, m), 5.46 (2H, m), 4.25–3.30 (4H, m), 3.44 (3H, s), 3.16 (2H, m), 2.89 (2H, q, 7.3 Hz), 2.65 (1H, m), 2.30 (1H, m), 2.15–1.80 (4H, m), 1.19 (3H, t, 7.3 Hz).

EXAMPLE 41

(2S,3S)-N-(5-Trifluoroacetylamino-2-methoxyphenyl)-methyl-2-diphenylmethyl-1-azabicyclo[2.2.2]octan-3-amine Mesylate The title compound was obtained using the same procedure as described in Example 38, except that 5-trifluoroacetylamino-2-methoxybenzaldehyde was substituted for 2-methoxy-5-methylthiobenzaldehyde. The yield of the product was 96%.

M.P. 148° C.

IR (KBr) cm$^{-1}$: 3430, 3050, 1610, 1500, 1200, 1060, 750, 710, 565.

$^1$H NMR (CDCl$_3$) δ: 9.50 (1H, br), 7.80 (1H, m), 7.5–7.1 (12H, m), 6.68 (1H, d, J=9.2 Hz), 4.68 (1H, m), 4.49 (1H, m), 3.80–3.50 (2H, m), 3.52 (3H, s), 3.50–3.20 (5H, m), 2.48 (3H, s), 2.42 (1H, m), 2.23 (1H, m), 1.99 (2H, m), 1.71 (1H, m).

EXAMPLE 42

(2S,3S)-N-(2-Methoxy-5-dimethylaminophenyl) methyl-2-diphenylmethyl-1-azabicyclo[2.2.2]octan-3-amine Mesylate The title compound was obtained using the same procedure as described in Example 38, except that 2-methoxy-5-dimethylaminobenzaldehyde was substituted for 2-methoxy-5-methylthiobenzaldehyde. The yield of the product was 75%.

M.P. 240° C.

IR (KBr) cm$^{-1}$: 3420, 2960, 1620, 1510, 1455, 1240, 1210, 1195, 1060, 785, 750, 710.

$^1$H NMR (CDCl$_3$) δ: 8.37 (1H, br), 7.45–7.20 (10H, m), 6.67 (2H, m), 6.38 (1H, m), 4.60 (1H, m), 4.23 (1H, m), 3.30–3.70 (5H, m), 3.49 (3H, s), 3.10–3.35 (2H, m), 2.86 (6H, s), 2.51 (3H, s), 2.42 (1H, m), 2.26 (1H, m), 2.15–1.50 (3H, m).

EXAMPLE 43

(2S,3S)-N-(5-Amino-2-methoxyphenyl)methyl-2-diphenylmethyl-1-azabicyclo[2.2.2]octan-3-amine Mesylate (2S,3S)-N-(5-Trifluoroacetylamino-2-methoxyphenyl)-methyl-2-diphenylmethyl-1-azabicyclo[2.2.2]octan-3-amine (1.52 g, 3 mmol) in CH$_2$Cl$_2$ (20 ml)/saturated NaHCO$_3$ (20 ml) was stirred vigorously for 8 hours. The CH$_2$Cl$_2$ layer was washed with water, dried over MgSO$_4$, and concentrated to give the title compound, which was converted to HCl salt by using HCl-ether. (Yield, 1.35 g, 81%).

M.P. 237° C.

IR (KBr) cm$^{-1}$: 3430, 2900, 1625, 1505, 1455, 1270, 1020, 755, 710.

$^1$H NMR (CDCl$_3$) δ: (free base) 7.45–7.05 (10H, m), 6.55 (1H, m), 6.47 (1H, m), 5.79 (1H, m), 4.50 (1H, d, 12 Hz), 3.70 (1H, m), 3.52 (3H, s), 3.50 (1H, d, 14 Hz), 3.28 (1H, d, 14 Hz), 3.20 (1H, m), 2.92 (1H, m), 2.79 (2H, m), 2.61 (1H, m), 2.04 (1H, m), 1.91 (1H, m), 1.65 (1H, m), 1.55 (1H, m), 1.28 (1H, m).

EXAMPLE 44

(2S,3S)-N-(2-Methoxy-5-methylsulfonylphenyl) methyl-2-diphenylmethyl-1-azabicyclo[2.2.2]octan-3-amine Mesylate The title compound of Example 38 (free amine) (1.20 g, 2.62 mmol) was treated with methanolic HCl to give the hydrochloride salt. Evaporation of the solvent gave crude (2S,3S)-N-(2-methoxy-5-methylthiophenyl)methyl-2-diphenylmethyl-1-azabicyclo[2.2.2]octan-3-amine dihydrochloride.

To a stirred and ice-cooled solution of (2S,3S)-N-(2-methoxy-5-methylthiophenyl)methyl-2-diphenylmethyl-1-azabicyclo[2.2.2]octan-3-amine dihydrochloride in methanol (25 mL) was added a solution of oxone (2.41 g) in water (25 mL). The reaction mixture was stirred at room temperature for 2.5 hours. The reaction mixture was basified to pH 10–11 with 1N NaOH aq. solution with ice-cooling, and extracted with CHCl$_3$ (80 mL×4). The combined organic layers were washed with brine (80 mL), dried (MgSO$_4$) and concentrated in vacuo to give crude (2S,3S)-N-(2-methoxy-5-methylsulfonylphenyl)methyl-2-diphenylmethyl-1-azabicyclo[2.2.2]octan-3-amine (white soap, 1.49 g). The residue was purified by chromatography on silica gel (60 g) with chloroform-methanol (20:1–10:1) to give (2S,3S)-N-(2-methoxy-5-methylsulfonylphenyl)methyl-2-diphenylmethyl-1-azabicyclo[2.2.2]octan-3-amine (1.08 g, 79%) as a white amorphous solid.

To a solution of (2S,3S)-N-(2-methoxy-5-methylsulfonylphenyl)methyl-2-diphenylmethyl-1-azabicyclo[2.2.2]octan-3-amine (400 mg, 0.82 mmol) in acetone (10 mL) was added methanesulfonic acid (0.41 mmol, 39.2 mg). The precipitated white solid was filtered off to give the title compound (218 mg, 30.3%, 1st crop).

M.P. 240°–241° C.

IR (KBr, free amine): 3430, 2940, 1597, 1493, 1449, 1350, 1306, 1256, 1186, 1128, 960, 820, 800, 754, 704 cm$^{-1}$.

$^1$H NMR (270 MHz, CDCl$_3$, ppm) (free amine): 7.77 (1H, dd, J=2.6, 8.4 Hz), 7.50 (1H, d, J=2.6 Hz), 7.37–7.03 (10H, m), 6.81 (1H, d, J=8.4 Hz), 4.47 (1H, d, J=12.1 Hz), 3.71 (1H, dd, J=7.7, 12.1 Hz), 3.62 (3H, s), 3.61 (1H, d, J=13.6 Hz), 3.21 (1H, d, J=13.6 Hz), 3.28–3.10 (1H, m), 3.01 (3H, s), 2.94 (1H, dd, J=4.4, 7.7 Hz), 2.83–2.74 (2H, m), 2.63 (1H, br.t, J=11.7 Hz), 2.10–2.03 (1H, m), 1.95–1.45 (3H, m), 1.35–1.20 (1H, m).

Anal. calc'd for C$_{29}$H$_{34}$N$_2$O$_2$S.CH$_3$SO$_3$H.2H$_2$O: C, 57.86; H, 6.80%; N, 4.50%. Found: C, 57.93%; H, 6.97%; N, 4.34%.

EXAMPLE 45

Cis-2- Diphenylmethyl)-N-((5-amino-2-methoxyphenyl)methyl)-1-azabicyclo[2.2.2]octan-3-amine To a 50 mL round-bottomed flask equipped with Dean-Stark trap, condenser and N$_2$ inlet were added 430 mg (2.38 mmol) 2-methoxy, 5-nitrobenzaldehyde, 578 mg (1.98 mmol) cis-2-(diphenylmethyl)-1-azabicyclo[2.2.2]octan-3-amine, 4 mg camphorsulfonic acid, and 10 mL toluene. The reaction was refluxed with removal of water for 14 hours, then cooled and evaporated. The residue was dissolved in 10 mL tetrahydrofuran, treated with 5 ml (10 mmol) of a 2.0M solution of borane/methyl sulfide in tetrahydrofuran, and refluxed for 3 days. The reaction was then cooled and evaporated, taken up to 10 mL ethanol, treated with 1 g sodium carbonate and 1 g cesium fluoride, and refluxed for 2 days. The reaction was cooled, partitioned between water and methylene chloride, and the organic layer was separated, washed with brine, dried over sodium sulfate, and evaporated. The residue was chromatographed on silica gel using acetonitrile/water/acetic acid as eluant, and the product fractions were isolated to afford 347 mg (41%) of an amorphous solid, which crystallized from isopropanol to give M.P. 164°–169° C.

$^1$H NMR ($\delta$, CDCl$_3$): 1.23 (m, 1H), 1.49 (m, 1H), 1.60 (m 1H), 1.90 (m, 1H), 2.03 (m, 1H), 2.60 (m, 2H), 2.75 (m, 2H), 2.89 (m, 1H), 3.20 (m, 1H), 3.39 (ABq, J$_{AB}$=16, $\Delta\nu$=62, 2H), 3.51 (s, 3H), 3.66 (dd, J=8,12, 1H), 4.49 (d, J=12, 1H), 5.78 (m, 1H), 6.4–6.6 and 7.0–7.4 (m, 13H).

$^{13}$C NMR ($\delta$, CDCl$_3$): 20.1, 24.8, 25.6, 42.1, 45.9, 49.3, 53.7, 54.3, 56.0, 61.8, 111.5, 114.0, 116.6, 125.9, 126.3, 127.6, 128.4, 129.0, 129.1, 139.7, 143.6, 145.7, 150.6.

IR (cm.$^{-1}$, KBr): 1620 and 1580.

MS (%): 428 (parent+1, 1), 291 (22), 260 (100), 136 (54), 106 (23).

Anal. calc'd for $C_{28}H_{33}N_3O$: C 78.65, H 7.78, N 9.83. Found: C 78.73, H 7.87, N 9.71.

The title compounds of Example 46 to 58 were prepared by a procedure similar to that described in Example 9.

EXAMPLE 46

(5-Isopropylsulfonyl-2-methoxybenzyl)-(2-phenylpiperidin-3-yl)amine dihydrochloride 17% yield, m.p. 278°–280° C. (dec.).

MS: m/e 402 (M$^+$), 398, 283, 275.

$^1$H NMR (CDCl$_3$, free base) $\delta$1.25 (dd, 6H), 1.35–2.2 (m, 6H), 2.8 (m, 2H), 3.15 (m, 1H), 3.25 (d, 1), 3.35 (d, 1H), 3.5 (s, 3H), 3.65 (d, 1H), 3.9 (d, 1H), 6.75 (d, 1H), 7.25 (m, 5H), 7.55 (s, 1H), 7.65 (dd, 1H).

Anal. calc'd for $C_{22}H_{30}N_2O_3S.2HCl$: C, 55.57; H, 6.78; N, 5.89. Found: C, 55.24; H, 6.54; N, 5.87.

EXAMPLE 47

N-Cyclopentyl-N-[4-methoxy-3-(2-phenylpiperidin-3-ylaminomethyl)phenyl]methanesulfonamide dihydrochloride hemihydrate 30% yield, m.p. 249°–252° C.

FABMS: m/e 458 (M$^{+1}$, 100%), 282 (10), 160 (55%).

$^1$H NMR (CDCl$_3$, free base) $\delta$1.25–1.65 (m, 8H), 1.75–2.05 (m, 5H), 2.15 (d, 1H), 2.8 (m, 2H), 2.9 (s, 3H), 3.25 (d, 1H), 3.35 (d, 1H), 3.5 (s, 3H), 3.7 (d, 1H), 3.9 (d, 1H), 4.45 (m, 1H), 6.65 (d, 1H), 6.9 (d, 1H), 7.05 (dd, 1H), 7.25 (m, 5H).

Anal. calc'd for $C_{25}H_{35}N_3O_3S.2HCl.1/2H_2O$: C, 55.65; H, 7.10; N, 7.79. Found: C, 55.69; H, 6.55; N, 7.78.

EXAMPLE 48

N-Cyclohexylmethyl-N-[4-methoxy-3-(2-phenylpiperidin-3-ylaminomethyl)phenyl]methanesulfonamide dihydrochloride hydrate 21% yield, m.p. 255°–256° C. (dec.).

FABMS: m/e 486 (M$^{+1}$), 408.

$^1$H NMR (CDCl$_3$, free base) $\delta$0.9–2.2 (m, 17H), 2.7–2.9 (m, 5H), 3.2–3.5 (m, 5H), 3.5 (s, 3H), 3.6 (d, 1H), 3.7 (d, 1H), 3.9 (d, 1H), 6.7 (d, 1H), 7.0 (d, 1H), 7.3 (dd, 1H), 7.4 (m, 5H).

Anal. calc'd for $C_{27}H_{39}N_3O_3S.2HCl.3/4H_2O$: C, 56.68; H, 7.49; N, 7.34. Found: C, 56.63; H, 7.11; N, 7.59.

EXAMPLE 49

(5-Methoxy-2-methyl-1-methylsulfonyl-2,3-dihydro-1H-indol-6-ylmethyl)-(2-phenylpiperidin-3-yl)amine dihydrochloride 16% yield, m.p. 257°–259° C.

FABMS: me 430 (M$^{+1}$, 10%), 254 (100%).

$^1$H NMR (CDCl$_3$, free base) $\delta$1.45 (dd, 3H), 1.65 (t, 1H), 1.8–2.2 (m, 4H), 2.6 (m, 1H), 2.75 (d, 3H), 2.85 (m, 1H), 3.3 (m, 1H), 3.4 (d, 3H), 3.45 (m, 1H), 3.65 (m, 1H), 3.9 (d, 1H), 4.4 (m, 1H), 6.55 (d, 1H), 7.15 (d, 1H), 7.25 (m, 5H).

Anal. calc'd for $C_{23}H_{31}N_3O_3S.2HCl$: C, 54.97; H, 6.22; N, 8.36. Found: C, 54.76; H, 6.45; N, 8.20.

EXAMPLE 50

1-[5-Methoxy-6-(2-phenylpiperidin-3-ylaminomethyl)-2,3-dihydroindol-1-yl]-heptan-1-one dihydrochloride hemihydrate 7% yield, m.p. 170°–172° C.

FABMS: m/e 450 (M$^{+1}$, 100%), 274, 160.

$^1$H NMR (CDCl$_3$, free base ) $\delta$0.9 (t, 3H), 1.25–1.45 (m, 6H), 1.5–1.8 (m, 3H), 1.85–2.25 (m, 4H), 2.4 (t, 2H), 2.8 (m, 2H), 3.15 (t, 2H), 3.25 (m, 1H), 3.3 (s, 3H), 3.35 (d, 1H), 3.7 (d, 1H), 3.9 (d, 1H), 4.05 (t, 2H), 6.5 (s, 1H), 7.25 (m, 5H), 8.0 (s, 1H).

Anal. calc'd for $C_{28}H_3N_3O_2.2HCl.1/2H_2O$: C, 63.27; H, 7.96; N, 7.90. Found: C, 63.33; H, 8.51; N, 8.19.

EXAMPLE 51

2,4-Dimethylthiazole-5-sulfonic acid [4-methoxy-3-(2-phenylpiperidin-3-ylaminomethyl)phenyl]-methylamide dihydrochloride hemihydrate 24% yield, m.p. 260°–264° C.

$^1$H NMR (CDCl$_3$, free base) $\delta$1.3–2.0 (m, 5H), 2.05 (d, 1H), 2.15 (s, 3H), 2.7 (s, 3H), 2.8 (m, 2H), 3.15 (s, 3H), 3.25 (d, 1H), 3.35 (d, 1H), 3.45 (s, 3H), 3.6 (d, 1H), 3.85 (d, 1H), 6.55 (d, 1H), 6.8 (d, 1H), 6.95 (dd, 1H), 7.25 (m, 5H).

Anal. calc'd for $C_{25}H_{32}N_4O_3.2HCl.1/2H_2O$: C, 51.54; H, 6.06; N, 9.62. Found: C, 51.31; H, 5.79; N, 9.76.

EXAMPLE 52

N-(4,5-dimethylthiazol-2-yl)-N-[4-methoxy-3(2-phenylpiperidin-3-ylaminomethyl)phenyl]methanesulfonamide dihydrochloride hemihydrate 40% yield, m.p. 247°–249° C.

FABMS: m/e 501 (M$^{+1}$), 421, 381, 247 (100%).

$^1$H NMR (CDCl$_3$, free base) $\delta$1.4 (d, 1H), 1.6 (t, 1H), 1.75 (m, 2H), 1.9 (m, 1H), 2.15 (d, 1H), 2.3 (m, 6H), 2.85 (m, 2H), 3.25 (d, 1H), 3.35 (d+s, 4H), 3.55 (s, 3H), 3.7 (d, 1H), 3.9 (d, 1H), 6.7 (d, 1H), 7.15 (d, 1H), 7.25 (m, 6H).

Anal. calc'd for $C_{25}H_{32}N_4O_3S_2.2HCl.1/2H_2O$: C, 51.54; H, 6.06; N, 9.62. Found: C, 51.87; H, 5.81; N, 9.55.

EXAMPLE 53

{5-[(4,5-dimethylthiazol-2-yl)methylamino]-2-methoxybenzyl}-(2-phenylpiperidin-3-yl)amine trihydrochloride hydrate 26% yield, m.p. 220°–225° C.

MS: m/e 436 (M$^+$, 16%), 317 (45%), 262 (100%).

¹H NMR (CDCl₃, free base) δ1.5 (m, 1H), 1.6 (m, 1H), 1.9 (m, 1H), 2.1 (s, 3H), 2.2 (s, 3H), 2.8 (m, 2H), 3.2 (m, 1H), 3.3 (s, 3H), 3.4 (d, 1H), 3.5 (s, 3H), 3.6 (d, 1H), 3.9 (d, 1H), 6.4 (d, 1H), 6.9 (d, 1H), 7.1 (q, 1H), 7.4 (m, 5H).

Anal. calc'd for $C_{25}H_{32}N_4OS \cdot HCl \cdot 3/2H_2O$: C, 52.40; H, 6.68; N, 9.78. Found: C, 52.12; H, 6.64; N, 9.55.

EXAMPLE 54

{5-[(4,5-dimethylthiazol-2-ylamino)-2-methoxybenzyl]-(2-phenylpiperidin-3-yl)amine trihydrochloride 28% yield, m.p. 272°–275° C.

MS: m/e 422 (M⁺, 40%), 303 (54%), 248 (100%).

¹H NMR (CDCl₃, free base) δ1.35–2.15 (m, 7H), 2.18 (s, 3H), 2.23 (s, 3H), 2.8 (m, 2H), 3.28 (d, 1H), 3.4 (d, 1H), 3.5 (s, 3H), 3.65 (d, 1H), 3.9 (d, 1H), 6.65 (d, 1H), 6.75 (d, 1H), 7.15 (dd, 1H), 7.3 (m, 5H).

Anal. calc'd for $C_{24}H_{30}N_4OS \cdot 3HCl$: C, 54.19; H, 6.25; N, 10.53. Found: C, 53.91; H, 6.39; N, 10.27.

EXAMPLE 55

{[4-Methoxy-3-(2-phenylpiperidin-3-ylaminomethyl) phenyl]-methyl-sulfamoyl}-acetic acid ethyl ester 48% yield, m.p. 245°–248° C.

MS: m/e 475 (M⁺, 5%) 356, 175, 150 (100%).

¹H NMR (CDCl₃, free base) δ1.3 (t, 3H), 1.3502.15 (m, 6H), 2.8 (m, 2H), 3.3 (d, 1H), 3.35 (s, 3H), 3.4 (d, 1H), 3.5 (s, 3H), 3.65 (d, 1H), 3.9 (d, 3H), 4.3 (q, 2H), 6.7 (d, 1H), 7.15 (d, 1H), 7.35 (m, 6H).

EXAMPLE 56

2-Hydroxyethanesulfonic acid [4-methoxy-3-(2-phenylpiperidin-3-ylaminomethyl)phenyl]-methylamide hydrochloride 4% yield, m.p. 255°–260° C. (dec.).

MS: m/e (433, M⁺), 314 (85%), 258 (100%).

¹H NMR (CDCl₃, free base) δ2.55 (bs, 4H), 2.75 (t, 1H), 2.85 (m, 1H), 3.15 (t, 2H), 3.2 (s, 3H), 3.35 (d, 1H), 3.5 (s, 3H), 3.65 (d, 1H), 3.9 (d, 1H), 3.95 (t, 2H), 6.65 (d, 1H), 7.1–7.4 (m, 7H).

Anal. calc'd for $C_{22}H_{31}N_3O_4S \cdot HCl$: C, 52.17; H, 6.57; N, 8.29. Found: C 51.89, N 6.27, N 7.95.

EXAMPLE 57

N-(3,4-Dichlorobenzyl)-N-[4-methoxy-3-(2-phenylpiperidin-3-ylaminomethyl)phenyl]-methanesulfonamide dihydrochloride hydrate 13% yield, m.p. 240°–243° C. (dec.).

MS: m/e 548 (M⁺¹, 8%), 428 (30), 159 (100).

¹H NMR (CDCl₃, free base) δ1.35–2.15 (m, 6H), 2.65 (m, 1H), 2.8 (t, 1H), 2.85 (s, 3H), 3.25 (d, 1H), 3.35 (d, 1H), 3.5 (s, 3H), 3.65 (d, 1H), 3.9 (d, 1H), 4.65 (q, 2H), 6.6 (d, 1H), 6.9 (d, 1H), 7.0 (dd, 1H), 7.15 (dd, 1H), 7.2–7.4 (m, 7H).

Anal. calc'd for $C_{27}H_{31}Cl_2N_3O_3S \cdot 1HCl \cdot 2/3H_2O$: C, 51.19; H, 5.46; N, 6.63. Found: C, 51.17; H, 5.33; N, 6.48.

EXAMPLE 58

4,5-Dimethylthiazole-2-sulfonic acid methyl-[3-(2-phenylpiperidin-3-yl-aminomethyl)-4-trifluoromethoxyphenyl]-amide trihydrochloride hydrate.

12% yield, m.p. 239°–240° C. (dec.),

MS: m/e 555 (M⁺¹), 380.

¹H NMR (CDCl₃, free base) δ1.5 (m, 1H), 1.7 (m, 1H), 1.9 )m, 4H), 2.1 (m, 1H), 2.2 (s, 3H), 2.7 (s, 3H), 2.8 (m, 2H), 3.2 (S,3H), 3.3 (m, 1H), 3.5 (q, 2H), 3.9 (d, 1H), 7.0 (m, 3H), 7.2 (m, 5H).

Anal. calc'd for $C_{25}H_{29}F_3N_4O_3S_2 \cdot 3HCl \cdot H_2O$: C, 44.09; H, 4.88; N, 8.23. Found: C, 44.36; H, 4.95; N, 8.51.

The title compounds of examples 59–62 were prepared by a procedure similar to that of Example 38C, starting with the appropriate aldehyde in place of 2-methoxy-5-methylthiobenzaldehyde.

EXAMPLE 59

(2S,3S)-3-[2-Methoxy-5-(N-acethyl-N-methylamino)benzyl-amino]-2-diphenylmethyl-1-azabicyclo[2.2.2]octane dihydrochloride M.p.: 232°–234° C. (AcOEt).

IR(KBr): 3430, 3055, 3020, 1648, 1500, 1386, 1244, 709 cm⁻¹.

¹H NMR (270 MHz, CDCl₃, free amine): 7.36–7.07 (m, 10H), 6.95 (dd, J=8.6, 2.6 Hz, 1H), 6.71 (d, J=8.6 Hz, 1H), 6.37 (d, J=2.6 Hz, 1H), 4.49 (d, J=12.1 Hz, 1H), 3.78–3.71 (m, 1H), 3.65–3.60 (m, 1H), 3.63 (s, 3H), 3.28–3.23 (m, 2H), 3.20 (s, 3H), 2.93 (dd, J=7.7, 4.4 Hz, 1H), 2.81 (m, 2H), 2.68 (m, 1H), 2.04 (m, 1H), 1.82 (s, 3H), 1.95–1.29 (m, 5H).

EXAMPLE 60

(2S,3S)-3-[2-Methoxy-5-(N-methyl-N-trifluoroacetylamino)benzylamino]-2-diphenylmethyl-1-azabicyclo[2.2.2]octane dihydrochloride ¹H NMR (270 MHz, CDCl₃, ppm) (free amine): 7.38–7.04 (m, 10H), 7.01 (dd, J=2.6, 8.8 Hz, 1H), 6.69 (d, J=8.8 Hz, 1H), 6.42 (br.s, 1H), 4.48 (d, J=12.1 Hz, 1H), 3.77–3.55 (m, 2H), 3.61 (s, 3H), 3.44–3.15 (m, 2H), 3.28 (s, 3H), 2.89 (dd, J=4.0, 7.7 Hz, 1H), 2.86–2.60 (m, 3H), 2.05–1.82 (m, 2H), 1.75–1.40 (m, 2H), 1.38–1.20 (m, 1H).

IR (KBr, cm⁻¹) (free amine): 3360, 1699, 1598, 1499, 1465, 1451, 1248, 1203, 1150, 1112, 1071, 1038, 817, 754, 703.

EXAMPLE 61

(2S,3S)-3-[5-(N-Isopropyl)-N-methylsulfonylamino)-2-methoxybenzylamino]-2-diphenylmethyl-1-azabicyclo[2.2.2]octane dihydrochloride M.p.: 178°–179° C.

¹H NMR (270 MHz, CDCl₃, ppm) (free amine): 7.34–7.03 (m, 10H), 7.07 (dd, J=2.6, 8.8 Hz, 1H), 6.82 (d, J=2.6 Hz, 1H), 6.68 (d, J=8.8 Hz, 1H), 4.53 (sep, J=6.6 Hz, 1H), 4.49 (d, J=12.1 Hz, 1H), 3.76–3.63 (m, 1H), 3.62 (d, J=13.6 Hz, 1H), 3.53 (s, 3H), 3.30–3.13 (m, 1H), 3.23 (d, J=13.6 Hz, 1H), 2.97–2.86 (m, 1H), 2.93 (s, 3H), 2.84–2.58 (m, 3H), 2.11–2.02 (m, 1H), 2.00–1.40 (m,4H), 1.38–1.20 (m, 1H), 1.15 (dd, J=2.6, 6.6 Hz, 6H).

IR (KBr, cm⁻¹) (free amine): 3340, 1603, 1495, 1462, 1450, 1366, 1332, 1232, 1181, 1154, 1130, 1107, 1032, 982, 961, 815, 801, 755, 703.

EXAMPLE 62

(2S, 3S)-3-[2-Methoxy-5-(N-methyl-N-methylsulfonylamino)benzylamino]-2-diphenylmethyl-1-azabicyclo[2.2.2]octane monomethanesulfonate M.p.: 197°–203° C. (IPA-Hex).

IR (KBr): 3430, 2945, 1500, 1340, 1218, 1166, 1039, 746 cm$^{-1}$.

$^1$H NMR (270 MHz, CDCl$_3$, free amine): 7.35–7.07 (m, 11H), 6.82 (d, J=2.6 Hz, 1H), 6.68 (d, J=8.8 Hz, 1H), 4.49 (d, J=12.1 Hz, 1H), 3.76–3.67 (m, 1H), 3.61–3.53 (m, 1H), 3.54 (s, 3H), 3.26 (s, 3H), 3.26–3.18 (m, 2H), 2.93 (dd, J=7.7, 4.0 Hz, 1H), 2.83 (s, 3H), 2.82–2.77 (m, 2H), 2.65 (m, 1H), 2.06 (m, 1H), 1.91–1.55 (m, 4H), 1.34–1.23 (m, 1H).

We claim:

1. A compound of the formula wherein ring A is an aryl group selected from phenyl, naphthyl, thienyl, dihydroquinolinyl and indolinyl, and wherein the side chain containing NR$^2$R$^3$ is attached to a carbon atom of ring A;

W is hydrogen, (C$_1$–C$_6$)alkyl, S—(C$_1$–C$_3$)alkyl, halo or (C$_1$–C$_6$)alkoxy optionally substituted with from one to three fluorine atoms;

R$^1$ is selected from —S(O)$_v$—(C$_1$–C$_{10}$)alkyl wherein v is zero, one or two, —S(O)$_v$-aryl wherein v is zero, one or two, —O—aryl, —SO$_2$NR$^4$R$^5$ wherein each of R$^4$ and R$^5$ is, independently, (C$_1$–C$_6$)alkyl, or R$^4$ and R$^5$, together with the nitrogen to which they are attached, form a saturated ring containing one nitrogen and from 3 to 6 carbons,

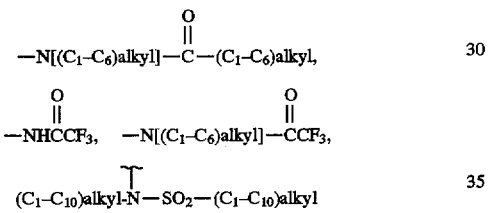

wherein one or both of the alkyl moieties may optionally be substituted with from one to three fluorine atoms, —N(SO$_2$—(C$_1$–C$_{10}$)alkyl)$_2$ and

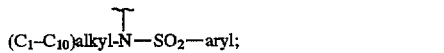

and wherein the aryl moieties of said —S(O)$_v$-aryl, —O-aryl and

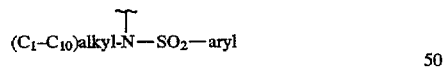

are independently selected from phenyl and benzyl and may optionally be substituted with from one to three substituents independently selected from (C$_1$–C$_4$)alkyl, (C$_1$–C$_4$)alkoxy and halo;

or R$^1$ is a group having the formula

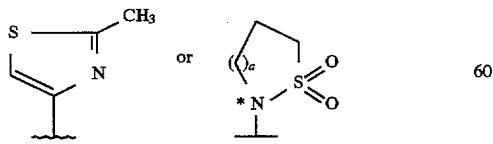

wherein a is 0, 1 or 2 and the asterisk represents a position meta to the R$^2$R$^3$NCH$_2$ side chain;

R$^2$ is hydrogen or —CO$_2$(C$_1$–C$_{10}$) alkyl;

R$^3$ is

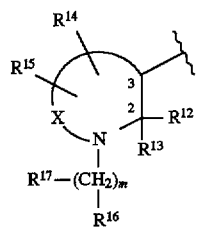

VII

X is (CH$_2$)$_q$ wherein q is 2 or 3 and any one of the carbon-carbon single bonds in said (CH$_2$)$_q$ may optionally be replaced by a carbon-carbon double bond, and wherein any one of the carbon atoms of said (CH$_2$)$_q$ may optionally be substituted with R$^{14}$, and wherein any one of the carbon atoms of said (CH$_2$)$_q$ may optionally be substituted with R$^{15}$;

m is an integer from 0 to 8, and any one of the carbon-carbon single bonds of (CH$_2$)$_m$, wherein both carbon atoms of such bond are bonded to each other and to another carbon atom in the (CH$_2$)$_m$ chain, may optionally be replaced by a carbon-carbon double bond or a carbon-carbon triple bond, and any one of the carbon atoms of said (CH$_2$)$_m$ may optionally be substituted with R$^{17}$;

R$^{12}$ is a radical selected from hydrogen, (C$_1$–C$_6$) straight or branched alkyl, (C$_3$–C$_7$)cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl-(C$_2$–C$_6$)alkyl, benzhydryl and benzyl, wherein the point of attachment on R$^{12}$ is a carbon atom unless R$^{12}$ is hydrogen, and wherein each of said aryl and heteroaryl groups and the phenyl moieties of said benzyl, phenyl-(C$_2$–C$_6$)alkyl and benzhydryl may optionally be substituted with one or more substituents independently selected from halo, nitro, (C$_1$–C$_{10}$)alkyl optionally substituted with from one to three fluorine atoms, (C$_1$–C$_{10}$)alkoxy optionally substituted with from one to three fluorine atoms, amino, hydroxy-(C$_1$–C$_6$)alkyl, (C$_1$–C$_6$)alkoxy-(C$_1$–C$_6$)alkyl, (C$_1$–C$_6$)-alkylamino,

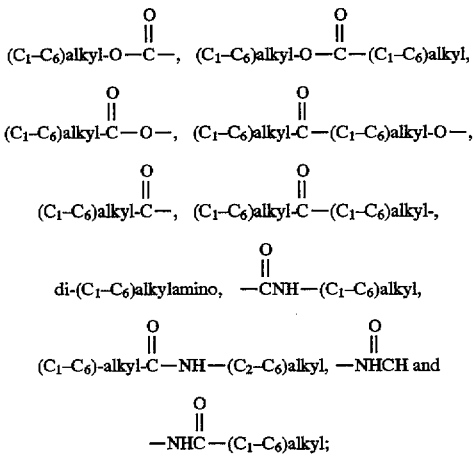

and wherein one of the phenyl moieties of said benzhydryl may optionally be replaced by naphthyl, thienyl, furyl or pyridyl;

$R^{13}$ is hydrogen, phenyl or $(C_1-C_6)$alkyl;

or $R^{12}$ and $R^{13}$, together with the carbon to which they are attached, form a saturated carbocyclic ring having from 3 to 7 carbon atoms wherein one of said carbon atoms that is neither the point of attachment of the spiro ring nor adjacent to it may optionally be replaced by oxygen, nitrogen or sulfur;

$R^{14}$ and $R^{15}$ are each independently selected from hydrogen, hydroxy, halo, amino, oxo (=O), cyano, hydroxy-$(C_1-C_6)$alkyl, $(C_1-C_6)$alkoxy-$(C_1-C_6)$alkyl, $(C_1-C_6)$alkylamino, di-$(C_1-C_6)$alkylamino,

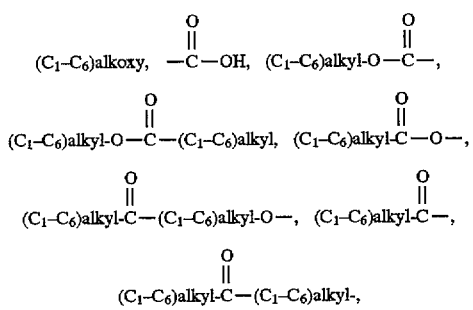

and the radicals set forth in the definition of $R^{12}$;

$R^{16}$ is

$NHCH_2R^{18}$, $SO_2R^{18}$, $CO_2H$ or one of the radicals set forth in any of the definitions of $R^{12}$, $R^{14}$ and $R^{15}$;

$R^{17}$ is oximino (=NOH) or one of the radicals set forth in any of the definitions of $R^{12}$, $R^{14}$ and $R^{15}$; and $R^{18}$ is $(C_1-C_6)$alkyl, hydrogen, phenyl or phenyl $(C_1-C_6)$alkyl;

with the proviso that (a) when m is 0, one of $R^{16}$ and $R^{17}$ is absent and the other is hydrogen, (b) when $R^{14}$ and $R^{15}$ are attached to the same carbon atom, then either each of $R^{14}$ and $R^{15}$ is independently selected from hydrogen, fluoro, $(C_1-C_6)$alkyl, hydroxy-$(C_1-C_6)$alkyl and $(C_1-C_6)$alkoxy-$(C_1-C_6)$alkyl, or $R^{14}$ and $R^{15}$, together with the carbon to which they are attached, form a $(C_3-C_6)$ saturated carbocyclic ring that forms a spiro compound with the nitrogen-containing ring to which they are attached; and (d) when $R^{14}$ or $R^{15}$ is attached to a carbon atom of X, then $R^{14}$ or $R^{15}$, respectively, must be a substituent wherein the point of attachment is a carbon atom;

or a pharmaceutically acceptable salt of such compound.

2. A compound according to claim 1, wherein $R^3$ is a group of the formula VII; $R^2$ is hydrogen; ring A is phenyl or indolinyl; W is $(C_1-C_3)$alkoxy optionally substituted with from one to three fluorine atoms; and $R^1$ is $S(O)_v$—$(C_1-C_{10})$alkyl wherein v is zero, one or two, $S(O)_v$-aryl wherein v is zero, one or two, —O-aryl,

wherein one or both of the alkyl moieties may optionally be substituted with from one to three fluorine atoms, —$N(SO_2$—$C_1-C_{10}$alkyl$)_2$ or

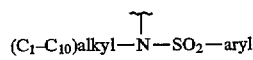

wherein said aryl is phenyl or benzyl and may optionally be substituted with from one to three substituents independently selected from $(C_1-C_4)$alkyl, $(C_1-C_4)$alkoxy and halo.

3. A compound according to claim 2, wherein $R^3$ is a group of the formula VII, each of $R^{13}$, $R^{14}$, $R^{15}$ and $R^{16}$ is hydrogen, m is zero and X is —$(CH_2)_3$—.

4. A compound according to claim 1, wherein the substituents at positions "2" and "3" of the nitrogen containing ring are in the cis configuration.

5. A compound according to claim 1, wherein $R^3$ is a group of the formula VII wherein $R^{12}$ and the substituent at position "3" of the nitrogen containing ring are in the cis configuration, ring A is phenyl, $R^{12}$ is phenyl, each of $R^2$, $R^{13}$, $R^{14}$, $R^{15}$ and $R^{16}$ is hydrogen, m is zero, X is —$(CH_2)_2$— or —$(CH_2)_3$— and $R^1$ is selected from $S(O)_v$—$(C_1-C_{10})$alkyl wherein v is zero, one or two, and

and di-$(C_1-C_6)$alkylamino.

6. A compound according to claim 5, wherein X is —$(CH_2)_2$— and W is $(C_1-C_6)$ alkoxy optionally substituted with from one to three fluorine atoms.

7. A compound according to claim 5, wherein X is —$(CH_2)_3$— and W is $(C_1-C_6)$ alkoxy optionally substituted with from one to three fluorine atoms.

8. A compound according to claim 3, wherein ring A is phenyl, W is selected from isopropoxy, $OCF_3$, $OCH_3$, $OCHF_2$ and $OCH_2CF_3$, and $R^1$ is selected from —$S(O)_v$—$(C_1-C_{10})$alkyl wherein v is zero, one or two, and

9. A compound according to claim 1, wherein $R^3$ is a group of the formula VII, m is zero, each of $R^{13}$, $R^{15}$, $R^{16}$ and $R^{17}$ is hydrogen, $R^{12}$ is phenyl,

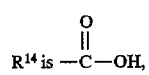

ring A is phenyl, W is $(C_1-C_3)$alkoxy and $R^1$ is selected from —$SCH_3$, $SO_2CH_3$, $SOCH_3$, $(C_1-C_6)$alkylamino and di-$(C_1-C_6)$alkyl-amino.

10. A compound according to claim 1, wherein said compound has the formula

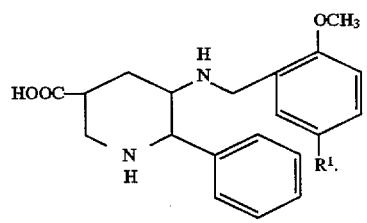

11. A compound according to claim 1, wherein said compound is selected from the group consisting of:
cis-3-(2-methylthiobenzyl)amino-2-phenylpiperidine;
cis-3-(5-chloro-2-methylthiobenzyl)amino-2-phenylpiperidine;

cis-3-(5-fluoro-2-methylthiobenzyl)amino-2-phenylpiperidine;

cis-3-(5-tert-butyl-2-methylthiobenzyl)amino-2-phenylpiperidine;

cis-3-(2-tert-butylthiobenzyl)amino-2-phenylpiperidine;

cis-3-(2-methylsufonylbenzyl)amino-2-phenylpiperidine;

cis-3-(2-methoxy-5-methylthiobenzyl)amino-2-phenylpiperidine;

cis-3-(2-difluoromethoxy-5-methylthiobenzyl)amino-2-phenylpiperidine;

cis-3-(2-methoxy-5-methylsulfinylbenzyl)amino-2-phenylpiperidine;

cis-3-(2-methoxy-5-methylsulfonylbenzyl)amino-2-phenylpiperidine;

cis-3-[2-methoxy-5-(N,N-diethylaminosulfonyl)-benzyl]amino-2-phenylpiperidine;

cis-3-[2-isopropoxy-5-(N,N-diethylaminosulfonyl)-benzyl]amino-2-phenylpiperidine;

cis-3-(2-(4-chlorophenylthio)benzyl)amino-2-phenylpiperidine;

cis-3-(2-phenyloxybenzylamino)-2-phenylpiperidine;

cis-3-(2-methoxy-5-phenyloxybenzylamino)-2-phenylpiperidine;

cis-3-[2-methoxy-5-(N-methyl-N-methanesulfonylamino)benzyl]amino-2-phenylpiperidine;

cis-3-[2-trifluoromethoxy-5-(N-methyl-N-methanesulfonylamino)benzyl]amino-2-phenylpiperidine;

cis-3-[2-isopropoxy-5-(N-methyl-N-methanesulfonylamino)benzyl]amino-2-phenylpiperidine;

cis-3-[2-cyclopentyloxy-5-(N-methyl-N-methanesulfonylamino)benzyl]amino-2-phenylpiperidine;

cis-3-[2-methoxy-5-(N-isopropyl-N-methanesulfonylamino)benzyl]amino-2-phenylpiperidine; p1 cis-3-[2-isopropoxy-5-(N-isopropyl-N-methanesulfonylamino)benzyl]amino-2-phenylpiperidine;

cis-3-[2-methoxy-5-(N-cyclopentyl-N-methanesulfonylamino)amino-2-phenylpiperidine;

cis-3-[2-methoxy-5-(N-methyl-N-trifluoromethanesulfonylamino)benzyl]amino-2-phenylpiperidine;

cis-3-[2-isopropoxy-5-(N-methyl-N-trifluoromethanesulfonylamino)benzyl]amino-2-phenylpiperidine;

cis-3-[2-methoxy-5-(N-methyl-N-isopropylsulfonylamino)benzyl]amino-2-phenylpiperidine;

cis-3-[2-methoxy-5-(N-methyl-N-(4-methylphenylsulfonyl)amino)benzyl]amino-2-phenylpiperidine;

cis-3-[2-isopropoxy-5-(N-methyl-N-(4-methylphenylsulfonyl)amino)benzyl]amino-2-phenylpiperidine;

cis-3-[2-methoxy-5-(N-methyl-N-phenylmethylsulfonylamino)benzyl]amino-2-phenylpiperidine;

cis-3-[2-trifluoromethoxy-5-(N,N-bis(methanesulfonyl)-amino)benzyl]amino-2-phenylpiperidine;

cis-3-[2-methoxy-5-(1,1-dioxo-2-isothiazolidinyl)benzyl]amino-2-phenyl-piperidine;

cis-3-[(2,3-dihydro-5-methoxy-1-methanesulfonyl-6-indolyl)methylamino]-2-phenylpiperidine;

cis-3-[(2,3-dihydro-5-methoxy-2-methyl-1-methanesulfonyl-6-indolyl)methylamino]-2-phenylpiperidine;

(2SR,3SR,4RS)-2-benzhydryl-4-(2-hydroxyethyl)-3-(2-methoxy-5-methylthiobenzyl)aminopyrrolidine;

(2SR,3SR,4RS)-2-benzhydryl-4-(2-hydroxyethyl)-3-(2-methoxy-5-(N-methyl-N-methanesulfonylamino)benzyl)aminopyrrolidine;

(2SR,3SR,4RS)-2-benzhydryl-4-(2-hydroxyethyl)-3-(2-methoxy-5-(N-thiazolidine-S,S-dioxide)benzyl)aminopyrrolidine and;

cis-3-(2-ethylthiophenyl)methylamino-2-phenylpiperidine.

12. A pharmaceutical composition for treating or preventing a condition selected from the group consisting of pain, migrane, anxiety, schizophrenia, asthma, rheumatoid arthritis, fibrositis or ulcerative colitis in a mammal, comprising an amount of a compound according to claim 1 effective in preventing or treating such condition and a pharmaceutically acceptable carrier.

13. A method of treating or preventing a condition selected from the group consisting of pain, migrane, anxiety, schizophrenia, asthma, rheumatoid arthritis, fibrositis or ulcerative colitis in a mammal, comprising administering to a mammal in need of such treatment or prevention an amount of a compound according to claim 1 effective in preventing or treating such condition.

14. A pharmaceutical composition for antagonizing the substance P receptor in a mammal, comprising a substance P receptor antagonizing effective amount of a compound according to claim 1 and a pharmaceutically acceptable carrier.

15. A method of antagonizing the substance P receptor in a mammal, comprising administering to said mammal a substance P receptor antagonizing effective amount of a compound according to claim 1.

16. A pharmaceutical composition for treating or preventing a condition in a mammal, the treatment or prevention of which is effected or facilitated by a decrease in substance P mediated neurotransmission, comprising an amount of a compound according to claim 1 effective in antagonizing the effect of substance P at its receptor site and a pharmaceutically acceptable carrier.

17. A method of treating or preventing a condition in a mammal, the treatment or prevention of which is effected or facilitated by a decrease in substance P mediated neurotransmission, comprising administering to a mammal in need of such treatment or prevention an amount of a compound according to claim 1, or a pharmaceutically acceptable salt thereof, effective in antagonizing the effect of substance P at its receptor site.

18. A pharmaceutical composition for treating or preventing a condition in a mammal, the treatment or prevention of which is effected or facilitated by a decrease in substance P mediated neurotransmission, comprising an amount of a compound according to claim 1, or a pharmaceutically acceptable salt thereof, effective in treating or preventing such condition and a pharmaceutically acceptable carrier.

19. A method of treating or preventing a condition in mammal, the treatment or prevention of which is effected or facilitated by a decrease in substance P mediated neurotransmission, comprising administering to a mammal in need of such treatment or prevention an amount of a compound according to claim 1 effective in treating or preventing such condition.

* * * * *

UNITED STATES PATENT AND TRADEMARK OFFICE
CERTIFICATE OF CORRECTION

PATENT NO. : 5,721,255
DATED : February 24, 1998
INVENTOR(S) : Harry R. Howard et al It is certified that error appears in the above-identified patent and that said Letters Patent is hereby corrected as shown below:

Claim 1, line 1, after "formula" insert--

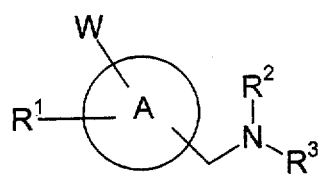

Signed and Sealed this

Twenty-sixth Day of September, 2000

Attest:

Q. TODD DICKINSON

*Attesting Officer*           *Director of Patents and Trademarks*